United States Patent
Erlich et al.

(10) Patent No.: US 10,570,394 B2
(45) Date of Patent: *Feb. 25, 2020

(54) DOUBLE-STRANDED RNA COMPOUNDS TO CASP2 AND USES THEREOF

(71) Applicant: Quark Pharmaceuticals, Inc., Fremont, CA (US)

(72) Inventors: Shai Erlich, Belmont, CA (US); James D. Thompson, Longmont, CO (US); Rabia Ozden, Edgewater, NJ (US); Elena Feinstein, Rehovot (IL)

(73) Assignee: Quark Pharmaceuticals, Inc., Newark, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/200,544

(22) Filed: Jul. 1, 2016

(65) Prior Publication Data

US 2016/0304879 A1 Oct. 20, 2016

Related U.S. Application Data

(63) Continuation of application No. 14/370,061, filed as application No. PCT/US2013/020012 on Jan. 3, 2013, now Pat. No. 9,382,542.

(60) Provisional application No. 61/596,231, filed on Feb. 8, 2012, provisional application No. 61/582,886, filed on Jan. 4, 2012.

(51) Int. Cl.
  *C12N 15/113* (2010.01)
  *A61M 5/178* (2006.01)
  *A61M 5/00* (2006.01)

(52) U.S. Cl.
  CPC ......... *C12N 15/1137* (2013.01); *A61M 5/002* (2013.01); *C12N 15/1135* (2013.01); *C12Y 304/22055* (2013.01); *C12N 2310/11* (2013.01); *C12N 2310/14* (2013.01); *C12N 2310/317* (2013.01); *C12N 2310/321* (2013.01); *C12N 2310/34* (2013.01); *C12N 2310/344* (2013.01); *C12N 2310/3521* (2013.01); *C12N 2320/32* (2013.01); *C12N 2320/35* (2013.01)

(58) Field of Classification Search
  None
  See application file for complete search history.

(56) References Cited

U.S. PATENT DOCUMENTS

| 6,444,776 | B1 | 9/2002 | Pang et al. | |
|---|---|---|---|---|
| 6,610,686 | B1* | 8/2003 | Enrico | A61K 31/496 514/229.8 |
| 7,863,436 | B2* | 1/2011 | Milner | A61K 38/005 536/23.1 |
| 8,614,309 | B2 | 12/2013 | Feinstein et al. | |
| 8,785,393 | B2* | 7/2014 | Hutchinson | A61K 31/435 514/20.5 |
| 9,121,020 | B2 | 9/2015 | Feinstein et al. | |
| 2003/0157030 | A1 | 9/2003 | Davis et al. | |
| 2004/0162255 | A1 | 8/2004 | Kaemmerer | |
| 2005/0186591 | A1* | 8/2005 | Bumcrot | C12N 15/113 435/6.16 |
| 2009/0162365 | A1* | 6/2009 | Feinstein | A61K 31/70 424/139.1 |
| 2009/0220572 | A1* | 9/2009 | Deschatelets | A61K 31/00 424/427 |
| 2010/0183696 | A1* | 7/2010 | Rodrigues | C12N 15/1138 424/423 |
| 2013/0123334 | A1 | 5/2013 | Feinstein et al. | |

FOREIGN PATENT DOCUMENTS

| WO | WO 2007/031091 | 3/2007 |
|---|---|---|
| WO | WO 2009/044392 | 4/2009 |
| WO | WO 2010/048352 | 4/2010 |
| WO | WO 2011/072091 | 6/2011 |
| WO | WO 2011/084193 | 7/2011 |

OTHER PUBLICATIONS

Mayo Clinic Glaucoma Symptoms. Retrieved from the internet: <URL:www.mayoclinic.org/diseases-conditions/glaucoma/basics/symptoms/con-20024042> [retrieved on Jun. 22, 2015] 3 pages.
Ahmed, Z. et al., "Ocular neuroprotection by siRNA targeting caspase-2", Cell Death and Disease, vol. 2:e173 (2011).
Nakamura, Yukari, International Application No. PCT/US2013/020012, Notification Concerning Transmittal of International Preliminary Report on Patentability, dated Jul. 17, 2014, 7 pages.
Macchia, Giovanni, International Application No. PCT/US2013/020012, International Search Report, dated May 21, 2013, 5 pages.

* cited by examiner

*Primary Examiner* — Tracy Vivlemore
(74) *Attorney, Agent, or Firm* — Fish & Richardson P.C.

(57) ABSTRACT

The present disclosure relates to methods of treating a patient suffering from or at risk of developing an ocular disease, disorder or injury, and includes treatment regimens using a double-stranded RNA compound that down-regulates CASP2 expression, or a pharmaceutically acceptable salt thereof.

9 Claims, 2 Drawing Sheets

Specification includes a Sequence Listing.

DOUBLE-STRANDED RNA COMPOUNDS TO CASP2 AND USES THEREOF

RELATED APPLICATIONS

This application is a continuation application of and claims priority to U.S. application Ser. No. 14/370,061, filed on Jul. 1, 2014, now U.S. Pat. No. 9,382,542, which is the U.S. National Stage of International Application No. PCT/US2013/020012, filed on Jan. 3, 2013, which was published in English under PCT Article 21(2), which claims the benefit of U.S. Provisional Application Ser. No. 61/582,886 filed Jan. 4, 2012 and of U.S. Provisional Application Ser. No. 61/596,231 filed Feb. 8, 2012, both entitled "Methods for Treating Eye Disorders", each of these applications is incorporated herein by reference in its entirety and for all purposes.

SEQUENCE LISTING

This application incorporates-by-reference nucleotide and/or amino acid sequences which are present in the file named "243-PCT1.ST25.txt", which is 25 kilobytes in size, and which was created Jan. 3, 2013 in the IBM-PCT machine format, having an operating system compatibility with MS-Windows.

FIELD OF THE INVENTION

Provided herein are compositions and methods of treating ocular disease, ocular disorder or ocular injury.

BACKGROUND OF THE INVENTION

There is a general lack of therapies for optic neuropathies. Glaucoma is treated in part by lowering intraocular pressure. Optic neuritis is managed by corticosteroids, but this does not affect the long-term course of the disease. Compressive optic neuropathy is treated by removing the tumor or aneurysm pressing on the optic nerve or chiasm. All other optic neuropathies, including nonarteritic anterior ischemic optic neuropathy (NAION), represent unmet medical needs. (Levin La. Axonal loss and neuroprotection in optic neuropathies. Can J Ophthalmol. 2007, 42(3):403-8).

PCT Publication Nos. WO 2008/050329 and WO 2009/044392 are directed to inhibitors of pro-apoptotic genes and disclose double-stranded RNA molecules targeting, inter alia, Caspase 2.

PCT Publication No. WO 2010/048352 is directed to compositions and methods of treating ocular diseases and discloses, inter alia, the chemically modified, double-stranded RNA compound QPI-1007 targeting the Caspase 2 gene.

Ahmed Z. et al., (Cell Death and Disease (2011) 2, e173) suggest that retinal ganglion cell (RGC) apoptosis induced by optic nerve injury in a rat model of optic nerve transection, involves activation of Caspase 2, and that synthetic double stranded RNA compounds designed to inhibit expression of Caspase 2 represent potential neuroprotective agents for intervention in human diseases involving RGC loss.

SUMMARY OF THE INVENTION

Provided herein are compounds and compositions for use in treating a subject and methods of treating a subject, wherein the subject is suffering from or at risk of developing an ocular disease, ocular disorder or ocular injury. The treatment comprises administering to the subject's eye a therapeutically effective dose of a double-stranded RNA compound that down regulates Caspase 2 (CASP2) expression in a single treatment or according to a treatment regimen having a dosing interval selected from one week, two weeks, one month, six weeks, two months and longer, or combinations thereof, wherein the regimen is maintained until the desired therapeutic effect is achieved for the subject. The doses provided herein present a favorable outcome to patients suffering from or at risk of developing an ocular disease, ocular disorder or ocular injury or in need of ocular neuroprotection, such as for example patients suffering from or at risk of developing non-arteritic anterior ischemic optic neuropathy (NAION) and other optic neuropathies, such as glaucoma, that result in the death of retinal ganglion cells (RGCs). The treatment regimens provided herein present a favorable outcome to patients suffering from or at risk of developing an ocular disease, ocular disorder or ocular injury including, and without being limited to, NAION and glaucoma.

Various aspects and embodiments provided herein involve use of a nucleic acid molecule, or a pharmaceutically acceptable salt thereof, that down-regulates expression of CASP2 in a subject's eye, that bind a nucleotide sequence (such as an mRNA sequence) or portion thereof, encoding CASP2, for example, the mRNA coding sequence (SEQ ID NO:3-5) for human CASP2, encoding one or more proteins or protein subunits exemplified by SEQ ID NO:6-8. In some embodiments, a nucleic acid molecule or a pharmaceutically acceptable salt thereof, that down regulates, or targets expression of the CASP2 gene is administered to an eye of the subject at a dose of about 0.05 mg to about 10 mg per eye, such as about 0.2 mg to about 6.0 mg per eye. In various embodiments the nucleic acid molecule or a pharmaceutically acceptable salt thereof is administered as an intravitreal (IVT) injection. In some embodiments the nucleic acid molecule or a pharmaceutically acceptable salt thereof is administered unilaterally. In some embodiments the nucleic acid molecule or a pharmaceutically acceptable salt thereof is administered bilaterally. In preferred embodiments the nucleic acid molecule is a double-stranded RNA (dsRNA) compound comprising an antisense strand and a sense strand. In various embodiments, the double-stranded RNA compound comprises an antisense strand with the sequence: 5' AGGAGUUCCACAUUCUGGC 3' (SEQ ID NO: 2) and a sense strand with the sequence 5' GCCAGAAUGUGGAACUCCU 3' (SEQ ID NO: 1).

In preferred embodiments, the double-stranded RNA compound (referred to herein as "QPI-1007") has the following structure:

```
                       (sense strand; SEQ ID NO: 1)
        5' iB - GCCAGAAUGUGGAACUCCU 3'

(antisense strand; SEQ ID NO: 2)
        3' CGGUCUUACACCUUGAGGA 5'
``` wherein each A, C, U and G is a nucleotide and each consecutive nucleotide is joined to the next nucleotide by a phosphodiester bond;

wherein each nucleotide is independently an unmodified ribonucleotide, a 2'-O-Methyl sugar modified ribonucleotide or a L-DNA nucleotide;

wherein the sense strand comprises, counting from the 5' terminus, an unmodified ribonucleotide at each of positions 1, 2, 3, 4, 5, 6, 7, 8, 9, 10, 11, 12, 13, 14, 15, 16, 17 and 19 and a L-deoxycytidine at position 18, and an inverted abasic deoxyribose cap (iB) covalently bound to the 5' terminus; and wherein the antisense strand comprises, counting from the 5' terminus, a 2'-O-Methyl sugar modified ribonucleotide at each of positions 2, 4, 6, 8, 11, 13, 15, 17 and 19 and an unmodified ribonucleotide at each of positions 1, 3, 5, 7, 9, 10, 12, 14, 16 and 18.

In preferred embodiments, there is provided a double-stranded RNA compound, or a pharmaceutically acceptable salt thereof, having the structure:

```
                        (sense strand; SEQ ID NO: 1)
         5' iB - GCCAGAAUGUGGAACUCCU 3'

(antisense strand; SEQ ID NO: 2)
         3' CGGUCUUACACCUUGAGGA 5'
``` wherein each A, C, U and G is a nucleotide and each consecutive nucleotide is joined to the next nucleotide by a phosphodiester bond;
wherein each nucleotide is independently an unmodified ribonucleotide, a 2'-O-Methyl sugar modified ribonucleotide or a L-DNA nucleotide;
wherein the sense strand comprises, counting from the 5' terminus, an unmodified ribonucleotide at each of positions 1, 2, 3, 4, 5, 6, 7, 8, 9, 10, 11, 12, 13, 14, 15, 16, 17 and 19 and a L-deoxycytidine at position 18, and an inverted abasic deoxyribose cap (iB) covalently bound to the 5' terminus;
wherein the antisense strand comprises, counting from the 5' terminus, a 2'-O-Methyl sugar modified ribonucleotide at each of positions 2, 4, 6, 8, 11, 13, 15, 17 and 19 and an unmodified ribonucleotide at each of positions 1, 3, 5, 7, 9, 10, 12, 14, 16 and 18;
for use in the treatment of a patient suffering from or at risk of developing an ocular disease, an ocular disorder or an ocular injury;
wherein the compound, or salt thereof, is administered to the patient's eye at a dose of about 0.05 mg to about 10 mg per eye.

In various embodiments, QPI-1007 is to be administered to a patient's eye at a dose of about 0.05 mg to about 10 mg per eye, at a dose of about 0.2 mg to about 6.0 mg per eye or at a dose of about 2.4 mg to about 6.0 mg per eye.

In various embodiments, the double-stranded RNA compound is administered to the patient's eye at a dose of about 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, 2.5 mg, 2.6 mg, 2.7 mg, 2.8 mg, 2.9 mg, 3.0 mg, 3.1 mg, 3.2 mg, 3.3 mg, 3.4 mg, 3.5 mg, 3.6 mg, 3.7 mg, 3.8 mg, 3.9 mg, 4.0 mg, 4.1 mg, 4.2 mg, 4.3 mg, 4.4 mg, 4.5 mg, 4.6 mg, 4.7 mg, 4.8 mg, 4.9 mg, 5.0 mg, 5.1 mg, 5.2 mg, 5.3 mg, 5.4 mg, 5.5 mg, 5.6 mg, 5.7 mg, 5.8 mg, 5.9 mg, 6.0 mg, 6.1 mg, 6.2 mg, 6.3 mg, 6.4 mg, 6.5 mg, 6.6 mg, 6.7 mg, 6.8 mg, 6.9 mg, 7.0 mg, 7.1 mg, 7.2 mg, 7.3 mg, 7.4 mg, 7.5 mg, 7.6 mg, 7.7 mg, 7.8 mg, 7.9 mg, 8.0 mg, 8.1 mg, 8.2 mg, 8.3 mg, 8.4 mg, 8.5 mg, 8.6 mg, 8.7 mg, 8.8 mg, 8.9 mg, 9.0 mg, 9.1 mg, 9.2 mg, 9.3 mg, 9.4 mg, 9.5 mg, 9.6 mg, 9.7 mg, 9.8 mg, 9.9 mg or 10.0 mg.

In certain embodiments of the compound for use or the method of treating, the double-stranded RNA compound is administered at a dose of about 0.2 mg per eye. In some embodiments of the compound for use or the method of treating, the double-stranded RNA compound is administered at a dose of 0.2 mg per eye.

In certain embodiments of the compound for use or the method of treating, the double-stranded RNA compound is administered at a dose of about 0.6 mg per eye. In some embodiments of the compound for use or the method of treating, the double-stranded RNA compound is administered at a dose of 0.6 mg per eye.

In certain embodiments of the compound for use or the method of treating, the double-stranded RNA compound is administered at a dose of about 1.2 mg per eye. In some embodiments of the compound for use or the method of treating, the double-stranded RNA compound is administered at a dose of 1.2 mg per eye.

In certain embodiments of the compound for use or the method of treating, the double-stranded RNA compound is administered at a dose of about 2.4 mg per eye. In some embodiments of the compound for use or the method of treating, the double-stranded RNA compound is administered at a dose of 2.4 mg per eye.

In certain embodiments of the compound for use or the method of treating, the double-stranded RNA compound is administered at a dose of about 4.8 mg per eye. In some embodiments of the compound for use or the method of treating, the double-stranded RNA compound is administered at a dose of 4.8 mg per eye.

In certain embodiments of the compound for use or the method of treating, the double-stranded RNA compound is administered at a dose of about 6.0 mg per eye. In some embodiments of the compound for use or the method of treating, the double-stranded RNA compound is administered at a dose of 6.0 mg per eye.

In preferred embodiments of the compound for use or the method of treating, the compound, or a pharmaceutically acceptable salt thereof, is prepared for intravitreal (IVT) injection. In preferred embodiments of the compound for use or the method of treating, the compound, or a pharmaceutically acceptable salt thereof, is administered as an intravitreal (IVT) injection. In some embodiments, the intravitreal (IVT) injection is administered in a single treatment. In some embodiments of the compound for use or the method of treating, the treatment comprises multiple (i.e. 2, 3, 4, 5, 6 or more) administrations of the double-stranded RNA compound. In preferred embodiments, the treatment comprises a multiple dose regimen, for example multiple (i.e. 2, 3, 4, 5, 6 or more) consecutive administrations. In some embodiments, the multiple administrations comprise multiple intravitreal (IVT) injections. In some embodiments of the compound for use or the method of treating provided herein, the double-stranded RNA compound, or a pharmaceutically acceptable salt thereof, is administered as six (6) consecutive intravitreal (IVT) injections. As provided herein, the multiple administrations can occur at regular intervals or at irregular intervals. In preferred embodiments, the multiple administrations occur at regular intervals. As provided herein, the regular intervals are selected from the group consisting of about one week, two weeks, one month, six weeks, two months and longer than two months. In some embodiments, the regular intervals are of about one month. In preferred embodiments of the compound for use or the method of treating, the double-stranded RNA compound is administered as intravitreal (IVT) injections at regular intervals of one month for six (6) consecutive months.

In some embodiments of the compound for use or the method of treating, for example in the treatment of a chronic eye disease, the double-stranded RNA compound is administered as intravitreal (IVT) injections at regular intervals of one month or two months for more than six (6) months, for example up to 12 months, or 24 months or more.

In certain embodiments of the compound for use or the method of treating, the volume of a single intravitreal (IVT) injection is about 1 µl to about 200 µl (µl refers to microliter). In some embodiments, the injection volume is about 5 µl to about 200 µl. In some embodiments, the injection volume is about 20 µl to about 200 µl. In some embodiments, the injection volume is between about 50 µl to about 100 µl. In some embodiments, the volume of a single intravitreal (IVT) injection is 50 µl or 100 µl.

In various embodiments of the compound for use or the method of treating, the double-stranded RNA compound, or a pharmaceutically acceptable salt thereof, is useful in the treatment of a subject suffering from or at risk of developing an ocular disease, an ocular disorder or an ocular injury, including for example, visual field loss, visual acuity loss, neurodegeneration, increased intraocular pressure, an ischemic event, retinal injury or optic nerve injury. In some embodiments of the compound for use or the method of treating, the double-stranded RNA compound, or a pharmaceutically acceptable salt thereof, is useful in the treatment of a subject suffering from or at risk of developing retinal injury or optic nerve injury. In some embodiments provided herein, the retinal injury or optic nerve injury comprises ischemic or hypoxic injury. In some embodiments of the compound for use or the method of treating, the double-stranded RNA compound, or a pharmaceutically acceptable salt thereof, is useful in achieving neuroprotection in the eye of the subject, for example neuroprotection of the RGC and/or neuroprotection of the optic nerve. In some embodiments of the compound for use or the method of treating, the double-stranded RNA compound, or a pharmaceutically acceptable salt thereof, is useful in reducing or preventing visual field loss in the eye of the subject. In some embodiments of the compound for use or the method of treating, the double-stranded RNA compound, or a pharmaceutically acceptable salt thereof, is useful in reducing or preventing visual acuity loss in the eye of the subject.

In some embodiments of the compound for use or the method of treating, the double-stranded RNA compound, or a pharmaceutically acceptable salt thereof, is useful in increasing or enhancing visual acuity in the eye of the subject, in particular in the eye of a NAION or glaucoma patient.

In various embodiments of the compound for use or the method of treating, the ocular disease, ocular disorder, or ocular injury is selected from the group consisting of ocular neuropathy, elevated intraocular pressure (IOP), glaucoma, acute angle closure (AAC), acute angle closure glaucoma (AACG), primary angle closure disease (PACD), primary angle closure glaucoma (PACG), dry eye, Sjögrens Syndrome, diabetic retinopathy (DR), diabetic macular edema (DME), age related macular degeneration (AMD), optic neuritis, central retinal vein occlusion, brunch retinal vein occlusion, ischemic optic neuropathy, optic nerve atrophy, optic nerve injury, non-arteritic anterior ischemic optic neuropathy (NAION), retinopathy of prematurity (ROP), retinitis pigmentosa (RP), retinal degeneration, retinal ganglion degeneration, macular degeneration, hereditary optic neuropathy, Leber's hereditary optic neuropathy, metabolic optic neuropathy, neuropathy due to a toxic agent, all secondary glaucomas, ocular hypertension, normal tension glaucoma, and a neuropathy caused by an adverse drug reaction or a vitamin deficiency.

In certain embodiments of the compound for use or the method of treating, the ocular disease, ocular disorder or ocular injury is optic nerve atrophy. In some embodiments, the optic nerve atrophy is chronic optic nerve atrophy.

In certain embodiments of the compound for use or the method of treating, the ocular disease, ocular disorder or ocular injury is retinal degeneration.

In certain embodiments of the compound for use or the method of treating, the ocular disease, ocular disorder or ocular injury is non-arteritic anterior ischemic optic neuropathy (NAION). In some embodiments, the NAION is acute NAION. In some embodiments of the compound for use or the method of treating, the ocular disease, ocular disorder or ocular injury is NAION or acute NAION and the double-stranded RNA compound, or a pharmaceutically acceptable salt thereof, is administered to the patient's eye within 14 days of the onset of NAION symptoms. In some embodiments of the compound for use or the method of treating, the ocular disease, ocular disorder or ocular injury is NAION or acute NAION and the double-stranded RNA compound, or a pharmaceutically acceptable salt thereof, is administered to the patient's eye within 28 days of the onset of NAION symptoms. In certain embodiments of the compound for use or the method of treating, the ocular disease, ocular disorder or ocular injury is optic neuritis.

In some embodiments of the compound for use or the method of treating, the ocular disease, ocular disorder or ocular injury is glaucoma, for example, a primary glaucoma or a secondary glaucoma. In some embodiments, the glaucoma is a primary glaucoma selected from the group consisting of primary open angle glaucoma, normal-tension glaucoma, primary angle-closure glaucoma (PACG), acute angle-closure glaucoma (AACG) and angle-closure glaucoma. In some embodiments of the compound for use or the method, the ocular disease, ocular disorder or ocular injury is primary angle closure (PAC) or acute angle closure (AAC). In some embodiments, the glaucoma is secondary glaucoma selected from the group consisting of pseudoexfoliation glaucoma, pigmentary glaucoma, neovascular glaucoma, steroid-induced glaucoma, and treatment refractory glaucoma.

In certain embodiments of the compound for use or the method of treating, the ocular disease, ocular disorder or ocular injury is Leber's hereditary optic neuropathy.

In various embodiments of the compound for use or the method of treating provided herein, the double-stranded RNA compound is in a form of a pharmaceutically acceptable salt. In preferred embodiments, the pharmaceutically acceptable salt is a sodium salt. A sodium salt of the compound means any compound containing at least one sodium atom.

In various embodiments of the compound for use or the method of treating provided herein, the double-stranded RNA compound is present in a composition that comprises the compound and a pharmaceutically acceptable carrier. In some embodiments, the pharmaceutically acceptable carrier is sterile saline solution suitable for injection into the eye. In certain embodiments, the composition further comprises a preservative. In various embodiments, the composition is formulated as a cream, a foam, a paste, an ointment, an emulsion, a liquid solution, an eye drop, a gel, spray, a suspension, a microemulsion, microspheres, microcapsules, nanospheres, nanoparticles, lipid vesicles, liposomes, polymeric vesicles, a patch, or a contact lens. In preferred embodiments, the composition is formulated as a liquid solution. In some embodiments, the liquid solution is prepared for a single dose intravitreal (IVT) injection and the volume of a single dose IVT injection is between about 20 μl to about 200 μl, preferably 50 μl to about 100 μl. In some embodiments, the liquid solution is prepared for a single dose intravitreal (IVT) injection and the volume of a single dose IVT injection is 100 μl. In some embodiments, the liquid solution is prepared for a single dose intravitreal (IVT) injection and the volume of a single dose IVT injection is 50 μl.

In another aspect, provided herein is an injectable composition comprising a pharmacologically acceptable aqueous excipient and the double-stranded RNA compound described hereinabove and infra. In various embodiments provided herein, the injectable composition is for use in treatment of a patient suffering from or at risk for developing an ocular disease, an ocular disorder or an ocular injury and for administering to the patient's eye.

In another aspect provided herein is a sodium salt of a double-stranded RNA compound targeting Caspase 2 having the structure:

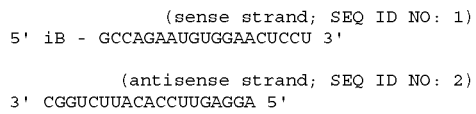

wherein each A, C, U and G is a nucleotide and each consecutive nucleotide is joined to the next nucleotide by a phosphodiester bond;
wherein the sense strand comprises, counting from the 5' terminus, an unmodified ribonucleotide at positions 1, 2, 3, 4, 5, 6, 7, 8, 9, 10, 11, 12, 13, 14, 15, 16, 17 and 19, a L-deoxycytidine at position 18, and an inverted abasic deoxyribose moiety 5' cap; and
wherein the antisense strand comprises, counting from the 5' terminus, a 2'-O-Methyl sugar modified ribonucleotide at positions 2, 4, 6, 8, 11, 13, 15, 17 and 19 and an unmodified ribonucleotide at positions 1, 3, 5, 7, 9, 10, 12, 14, 16 and 18;
wherein the molecular formula is $C_{375} H_{439} N_{143} Na_{37} O_{266} P_{37}$; and
wherein the molecular weight is 13,202 Da.

In another aspect, provided herein is a pharmaceutical composition comprising a sodium salt of double-stranded RNA compound having the structure:

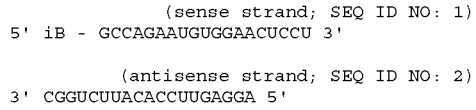

wherein each A, C, U and G is a nucleotide and each consecutive nucleotide is joined to the next nucleotide by a phosphodiester bond;
wherein the sense strand comprises, counting from the 5' terminus, an unmodified ribonucleotide at positions 1, 2, 3, 4, 5, 6, 7, 8, 9, 10, 11, 12, 13, 14, 15, 16, 17 and 19, a L-deoxycytidine at position 18, and an inverted abasic deoxyribose moiety 5' cap; and
wherein the antisense strand comprises, counting from the 5' terminus, a 2'-O-Methyl sugar modified ribonucleotide at positions 2, 4, 6, 8, 11, 13, 15, 17 and 19 and an unmodified ribonucleotide at positions 1, 3, 5, 7, 9, 10, 12, 14, 16 and 18;
wherein the molecular formula is $C_{375} H_{439} N_{143} Na_{37} O_{266} P_{37}$ and the molecular weight is 13,202 Da; and
a pharmaceutically acceptable excipient or carrier or mixture thereof.

In various embodiments, the sodium salt of the double-stranded RNA compound as provided herein is present in the composition at an amount of about 0.05 mg to about 10.0 mg per dosage form. In some embodiments, the sodium salt of the double-stranded RNA compound as provided herein is present in the composition in an amount of 0.05 mg to 10.0 mg per dosage unit.

In certain embodiments of the pharmaceutical composition, the sodium salt of QPI-1007 is present in the composition in an amount of about 0.1 mg to about 8.0 mg per dosage form, or at in an amount of 0.1 mg to 8.0 mg. In certain embodiments, the sodium salt of QPI-1007 is present in the composition in an amount of about 0.2 mg to about 6.0 mg per dosage form, or at in an amount of 0.2 mg to 6.0 mg.

In certain embodiments of the pharmaceutical composition, the sodium salt of QPI-1007 is present in the composition in an amount of about 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, 2.5 mg, 2.6 mg, 2.7 mg, 2.8 mg, 2.9 mg, 3.0 mg, 3.1 mg, 3.2 mg, 3.3 mg, 3.4 mg, 3.5 mg, 3.6 mg, 3.7 mg, 3.8 mg, 3.9 mg, 4.0 mg, 4.1 mg, 4.2 mg, 4.3 mg, 4.4 mg, 4.5 mg, 4.6 mg, 4.7 mg, 4.8 mg, 4.9 mg, 5.0 mg, 5.1 mg, 5.2 mg, 5.3 mg, 5.4 mg, 5.5 mg, 5.6 mg, 5.7 mg, 5.8 mg, 5.9 mg, 6.0 mg, 6.1 mg, 6.2 mg, 6.3 mg, 6.4 mg, 6.5 mg, 6.6 mg, 6.7 mg, 6.8 mg, 6.9 mg, 7.0 mg, 7.1 mg, 7.2 mg, 7.3 mg, 7.4 mg, 7.5 mg, 7.6 mg, 7.7 mg, 7.8 mg, 7.9 mg, 8.0 mg, 8.1 mg, 8.2 mg, 8.3 mg, 8.4 mg, 8.5 mg, 8.6 mg, 8.7 mg, 8.8 mg, 8.9 mg, 9.0 mg, 9.1 mg, 9.2 mg, 9.3 mg, 9.4 mg, 9.5 mg, 9.6 mg, 9.7 mg, 9.8 mg, 9.9 mg, or 10.0 mg per dose form, or in an amount of 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, 2.5 mg, 2.6 mg, 2.7 mg, 2.8 mg, 2.9 mg, 3.0 mg, 3.1 mg, 3.2 mg, 3.3 mg, 3.4 mg, 3.5 mg, 3.6 mg, 3.7 mg, 3.8 mg, 3.9 mg, 4.0 mg, 4.1 mg, 4.2 mg, 4.3 mg, 4.4 mg, 4.5 mg, 4.6 mg, 4.7 mg, 4.8 mg, 4.9 mg, 5.0 mg, 5.1 mg, 5.2 mg, 5.3 mg, 5.4 mg, 5.5 mg, 5.6 mg, 5.7 mg, 5.8 mg, 5.9 mg, 6.0 mg, 6.1 mg, 6.2 mg, 6.3 mg, 6.4 mg, 6.5 mg, 6.6 mg, 6.7 mg, 6.8 mg, 6.9 mg, 7.0 mg, 7.1 mg, 7.2 mg, 7.3 mg, 7.4 mg, 7.5 mg, 7.6 mg, 7.7 mg, 7.8 mg, 7.9 mg, 8.0 mg, 8.1 mg, 8.2 mg, 8.3 mg, 8.4 mg, 8.5 mg, 8.6 mg, 8.7 mg, 8.8 mg, 8.9 mg, 9.0 mg, 9.1 mg, 9.2 mg, 9.3 mg, 9.4 mg, 9.5 mg, 9.6 mg, 9.7 mg, 9.8 mg, 9.9 mg, or 10.0 mg per dose form.

In certain embodiments of the pharmaceutical composition, the sodium salt of QPI-1007 is present in the composition in an amount of about 0.2 mg per dose form, or in an amount of 0.2 mg per dose form.

In certain embodiments of the pharmaceutical composition, the sodium salt of QPI-1007 is present in the composition in an amount of about 0.6 mg per dose form, or in an amount of 0.6 mg per dose form.

In certain embodiments of the pharmaceutical composition, the sodium salt of QPI-1007 is present in the composition in an amount of about 1.2 mg per dose form, or in an amount of 1.2 mg per dose form.

In certain embodiments of the pharmaceutical composition, the sodium salt of QPI-1007 is present in the composition in an amount of about 2.4 mg per dose form, or in an amount of 2.4 mg per dose form.

In certain embodiments, the sodium salt of QPI-1007 is present in the composition in an amount of about 4.8 mg per dose form, or in an amount of 4.8 mg per dose form.

In certain embodiments of the pharmaceutical composition, the sodium salt of QPI-1007 is present in the composition in an amount of about 6.0 mg per dose form, or in an amount of 6.0 mg per dose form.

In certain embodiments of the pharmaceutical composition, the double-stranded RNA compound, or a pharmaceutically acceptable salt thereof, is formulated in a pharmaceutically acceptable excipient or carrier at a concentration of about 0.5 mg/mL to about 100.0 mg/mL, or at a concentration of 0.5 mg/mL to 100.0 mg/mL. In certain embodiments of the pharmaceutical composition, the double-stranded RNA compound, or a pharmaceutically acceptable salt thereof, is formulated in a pharmaceutically acceptable excipient or carrier at a concentration of about 1.0 mg/mL to about 80.0 mg/mL, or at a concentration of 1.0 mg/mL to 80.0 mg/mL In certain embodiments, the double-stranded RNA compound, or a pharmaceutically acceptable salt thereof, is formulated in a pharmaceutically acceptable excipient or carrier at a concentration of about 2.0 mg/mL to about 60.0 mg/mL, or at a concentration of 2.0 mg/mL to 60.0 mg/mL.

In certain embodiments of the pharmaceutical composition, the double-stranded RNA compound, or a pharmaceutically acceptable salt thereof, is present in the composition at a concentration of about 2.0 mg/mL, or at a concentration of 2.0 mg/mL. In certain embodiments, the double-stranded RNA compound, or a pharmaceutically acceptable salt thereof, is present in the composition at a concentration of about 12.0 mg/mL, or at a concentration of 12.0 mg/mL. In certain embodiments, the double-stranded RNA compound, or a pharmaceutically acceptable salt thereof, is present in the composition at a concentration of about 24.0 mg/mL, or at a concentration of 24.0 mg/mL. In certain embodiments, the double-stranded RNA compound, or a pharmaceutically acceptable salt thereof, is present in the composition at a concentration of about 48.0 mg/mL, or at a concentration of 48.0 mg/mL. In certain embodiments, the double-stranded RNA compound, or a pharmaceutically acceptable salt thereof, is present in the composition at a concentration of about 60.0 mg/mL, or at a concentration of 60.0 mg/mL In certain embodiments, the double-stranded RNA compound, or a pharmaceutically acceptable salt thereof, is present in the composition at a concentration of about 100.0 mg/mL, or at a concentration of 100.0 mg/mL In certain embodiments, the double-stranded RNA compound, or a pharmaceutically acceptable salt thereof, is present in the composition at a concentration of about 120.0 mg/mL, or at a concentration of 120.0 mg/mL.

In certain embodiments of the pharmaceutical composition, QPI-1007 or a sodium salt thereof, is formulated in a pharmaceutically acceptable excipient or carrier or mixture thereof at a concentration of about 60 mg/mL. In certain embodiments, QPI-1007, or a pharmaceutically acceptable salt thereof, is formulated in a preservative-free, sterile solution at a concentration of 60 mg/mL In certain embodiments the sterile solution is a phosphate-buffered saline.

In some embodiments, the compound for use described herein is present in a kit comprising the double-stranded RNA compound, or a pharmaceutically acceptable salt thereof, or the composition described hereinabove and infra, and instructions for use thereof. In various embodiments of the kit, the use is for treatment of an ocular disease, an ocular disorder or an ocular injury, for example, wherein the ocular injury includes ischemic injury, ischemia-reperfusion injury, mechanical injury, injury or interruption of nerve fibers and/or is associated with lack of supply of neurotrophic factor, or wherein the ocular disease, an ocular disorder or an ocular injury is associated with death of retinal ganglion cells (RGCs). In various embodiments of the kit, the disease is selected from the group of diseases and disorders described herein. In various embodiments of the kit, the kit contains dosage units of medication of the double-stranded RNA compound, or a pharmaceutically acceptable salt thereof, or the composition described herein.

In various embodiments, the kit for use in the treatment of an ocular disease, an ocular disorder or an ocular injury comprises the double-stranded RNA compound or a pharmaceutically acceptable salt thereof, or the composition described hereinabove and infra, packaged in a suitable sealed container; at least one syringe needle, suitable for intravitreal injection; and at least one syringe. In some embodiments of the kit, the syringe is a precisely calibrated syringe. In some embodiments of the kit, the needle is a self-sealing syringe needle, suitable for intravitreal injection. In some embodiments of the kit, the kit for use in the treatment of an ocular disease, an ocular disorder or an ocular injury comprises the double-stranded RNA compound or a pharmaceutically acceptable salt thereof, or the composition described hereinabove and infra, packaged in a suitable scaled container; at least one self-scaling syringe needle, suitable for intravitreal injection; and at least one precisely calibrated syringe. In various embodiments of the kit, the needle is selected from a 30-gauge, a 31-gauge, and a 32-gauge needle. In various embodiments, the kit further comprises printed informational material describing the double-stranded RNA compound or a pharmaceutically acceptable salt thereof, or the composition, its method of administration and any required safety and efficacy information as may be required by government regulations.

In a related aspect, provided are compositions or kits that include the QPI-1007 compound or a pharmaceutically acceptable salt thereof, packaged for use by a patient. The package may be labeled or include a package label or insert that indicates the content of the package and provides certain information regarding how the compound should be or can be used by a patient, for example the label may include dosing information and/or indications for use. In certain embodiments the contents of the label will bear a notice in a form prescribed by a government agency, for example the United States Food and Drug administration. In certain embodiments, the label may indicate that the compound is suitable for use in treating a patient suffering from a disease associated with increased expression of Caspase 2 and/or apoptosis of a retinal ganglion cell (RGC) and/or optic nerve damage; for example, the label may indicate that the compound is suitable for use in treating NAION or glaucoma; or for example the label may indicate that the compound or a pharmaceutically acceptable salt thereof, is suitable for use in treating an eye disease selected from the group consisting of ocular neuropathy, elevated intraocular pressure (IOP), glaucoma, acute angle closure (AAC), acute angle closure glaucoma (AACG), primary angle closure (PAC), primary angle closure glaucoma (PACG), dry eye, Sjögrens Syndrome, diabetic retinopathy (DR), diabetic macular edema (DME), age related macular degeneration (AMD), optic neuritis, central retinal vein occlusion, brunch retinal vein occlusion, ischemic optic neuropathy, optic nerve atrophy, optic nerve injury, non-arteritic anterior ischemic optic neuropathy (NAION), retinopathy of prematurity (ROP), retinitis pigmentosa (RP), retinal degeneration, retinal ganglion degeneration, macular degeneration, hereditary optic neuropathy, Leber's hereditary optic neuropathy, metabolic optic neuropathy, neuropathy due to a toxic agent, all secondary glaucomas, ocular hypertension, normal tension glaucoma, and a neuropathy caused by an adverse drug reaction or a vitamin deficiency.

DETAILED DESCRIPTION OF THE INVENTION

Definitions

Figure 1:
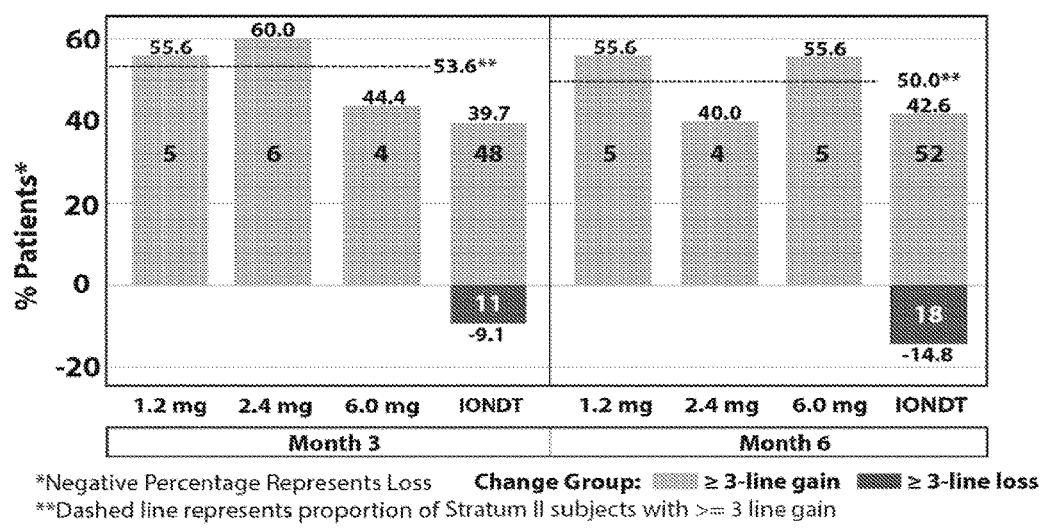
FIG. 1 is bar graph showing the proportion of NAION subjects who gained or lost ≥3 lines of VA after receiving a single IVT injection of QPI-1007 by cohort compared with historical controls at months 3 and 6.

For convenience certain terms employed in the specification, examples and claims are described herein.

It is to be noted that, as used herein, the singular forms "a", "an" and "the" include plural forms unless the content clearly dictates otherwise.

As used herein the term "about" with regard to a numerical value refers to the numerical value ±10%.

As used herein, the term "inhibit", "down-regulate", or "reduce" with respect to gene expression means the expression of the gene, or level of RNA molecules or equivalent RNA molecules encoding one or more proteins or protein subunits (e.g., mRNA), or activity of one or more proteins or protein subunits, is reduced below that observed in the absence of an inhibitory factor (such as a nucleic acid molecule, e.g., an siNA, for example having structural features as described herein); for example the expression may be reduced to 90%, 80%, 70%, 60%, 50%, 40%, 30%, 20%, 10%, 5% or less than that observed in the absence of an inhibitor.

"Nucleotide" is meant to encompass deoxyribonucleotides and ribonucleotides, which may be natural or synthetic and modified or unmodified. Nucleotides include known nucleotide analogues, which are synthetic, naturally occurring, and non-naturally occurring. Examples of such analogs include, without limitation, phosphorothioates, phosphoramidites, methyl phosphonates, chiral-methyl phosphonates, 2'-O-methyl ribonucleotides, and peptide-nucleic acids (PNAs). Modifications include changes to the sugar moiety, the base moiety and or the linkages between ribonucleotides in the oligoribonucleotide. As used herein, the term "ribonucleotide" encompasses natural and synthetic, unmodified and modified ribonucleotides and ribonucleotide analogs which are synthetic, naturally occurring, and non-naturally occurring. Modifications include changes to the sugar moiety, to the base moiety and/or to the linkages between ribonucleotides in the oligonucleotide.

A "mirror nucleotide" is a nucleotide with reversed chirality to the naturally occurring or commonly employed nucleotide, i.e., a mirror image (L-nucleotide) of the naturally occurring D-nucleotide, referred to as L-RNA for a mirror ribonucleotide. The L-ribonucleotide or L-deoxyribonucleotide may further comprise at least one sugar, base and or backbone modification. See U.S. Pat. No. 6,586,238. U.S. Pat. No. 6,602,858 discloses nucleic acid catalysts comprising at least one L-nucleotide substitution. Mirror nucleotide includes for example L-DNA (L-deoxyriboadenosine-3'-phosphate (mirror dA); L-deoxyribocytidine-3'-phosphate (mirror dC); L-deoxyriboguanosine-3'-phosphate (mirror dG); L-deoxyribothymidine-3'-phosphate (mirror dT) and L-RNA (L-riboadenosine-3'-phosphate (mirror rA); L-ribocytidine-3'-phosphate (mirror rC); L-riboguanosine-3'-phosphate (mirror rG); L-ribouridine-3'-phosphate (mirror dU).

Ocular Diseases

In various embodiments the double-stranded RNA compounds provided herein are useful in treating patients suffering from ocular diseases, disorders and injury in which neuroprotection of the optic nerve would be of benefit, for example, without being limited to, in treating ION, including NAION, glaucoma, including glaucomatous optic neuropathy, Leber's hereditary optic neuropathy (LHON), or Leber's optic atrophy.

The term "treatment" refers to both therapeutic treatment and prophylactic or preventative measures, wherein the object is to prevent, retard, or attenuate the related eye disorder as listed above. Those in need of treatment include those already experiencing the disease or condition, those prone to having the disease or condition, and those in which the disease or condition is to be prevented. The terms "prevent," "preventing," and "prevention" refer to delaying or precluding the onset of a disorder; and/or its attendant symptoms, in a subject or reducing a subject's risk of acquiring a disorder.

The term "subject" refers to an animal, preferably a mammal and including primates (e.g., human, monkey, chimpanzee, gorilla, and the like), The terms "subject" and "patient" are used interchangeably herein in reference, for example, to a mammalian subject, such as a human patient.

Although intravitreal injection is the preferred method of administration, other modes of administration are contemplated, including topical, subconjunctival and subtenon administration.

Optic nerve atrophy can be congenital or acquired. If congenital, it is usually hereditary with an onset of deterioration in childhood or adolescence (e.g. Leber's hereditary optic neuropathy (LHON), or Leber's optic atrophy, dominant optic atrophy or Kjer's optic neuropathy and numerous less common genetically related syndromes). Alternatively, congenital optic atrophy can be caused by a lack of oxygen during pregnancy, labor or in the immediate postnatal period. Some drugs taken during pregnancy are also associated with optic atrophy. Acquired optic atrophies result from multiple etiologies such as decreased blood supply to the eye or optic nerve (anterior ischemic optic neuropathy or posterior ischemic optic neuropathy), inflammation or swelling within the optic nerve (optic neuritis), and pressure against the optic nerve (such as from a tumor or glaucoma). Although less common, it can also be related to metabolic diseases (e.g., diabetes mellitus), trauma, or toxicity (caused by methanol, tobacco, or other poisons). It is also seen in vitamin B12 deficiency and Paget's disease of bone.

The most common optic neuropathy is glaucomatous optic neuropathy (aka glaucoma), distinguished by a distinctive and progressive excavation of the optic nerve head without significant pallor of the remaining neuroretinal rim. In glaucomatous optic neuropathy, retinal ganglion cells (RGCs) die.

The process of RGC death is thought to be biphasic, where a primary injury responsible for initiation of damage is followed by a slower secondary degeneration related to the noxious environment surrounding the degenerating cells. For example, retinal ischemia as a result of increased intraocular pressure may establish a cascade of changes that ultimately results in cell death. Hypoxia leads to excitotoxic levels of glutamate, which cause a rise in intra-cellular calcium, which in turn, leads to neuronal death due to apoptosis or necrosis. (Kaushik et al., Neuroprotection in glaucoma. J Postgrad Med. 2003, 49(1):90-5)

Increased intraocular pressure (IOP) (above 22 mmHg or 2.9 kPa) is a significant risk factor for developing glaucoma. However, significant variability exists with respect to sensitivity of the optic nerve to increased IOP with some patients developing nerve damage at a relatively low pressure, while others may have high pressure for years and yet never develop damage. Furthermore, while reducing IOP helps prevent glaucoma in some at-risk individuals (e.g., those with ocular hypertension) and also prevents progression of glaucoma in some individuals with existing disease, simply reducing IOP is not always effective. Moreover, achieving adequate pressure lowering may be difficult or associated with adverse effects (AE). On the other hand, neuroprotection is a process that attempts to preserve the cells that were spared during the initial insult, but are still vulnerable to damage. Although not yet available, a neuroprotective agent potentially could be of great use in arresting the progression of glaucoma.

Hypoxic injury of the optic nerve is not limited to glaucoma. Ischemic optic neuropathy (ION) is another important subtype of optic nerve atrophy that includes a variety of disorders associated with ischemia of the optic nerve. Posterior Ischemic Optic Neuropathy (PION) is a rare medical condition characterized by ischemic damage to the retrobulbar portion of the optic nerve. (Hayreh S S. Posterior ischaemic optic neuropathy: clinical features, pathogenesis, and management. Eye. 2004, 18(11):1188-206).

The more common form of ION, Anterior Ischemic Optic Neuropathy (AION) is the result of disturbances in blood flow through the posterior ciliary arteries leading to ischemic injury of optic nerve axons in the optic nerve head and subsequent loss of retinal ganglion cells. AION can be distinguished from PION by the fact that AION occurs spontaneously and unilaterally in patients with predisposing anatomy and cardiovascular risk factors. Furthermore, by definition, ION is termed anterior if disc edema is present acutely. (Biousse V, Newman N.J. Neuro-Ophthalmology Illustrated. New York, N.Y.: Thieme Medical Publishers; 2009).

After glaucoma, AION is the second most common optic nerve-related cause of permanent visual loss in adults. Clinically, AION is of two types:

1. Arteritic AION (A-AION): causes a severe loss of vision and is the primary cause of vision loss in patients with temporal arteritis (also called giant cell arteritis), a systemic disorder affecting primarily the elderly characterized by granulomatous (giant cells) inflammation of large- and medium-sized arteries. A-AION represents less than 6% of all cases of AION. (Miller et al., Walsh and Hoyt's Clinical Neuro-Ophthalmology: The Essentials. 2 ed. Philadelphia, Pa.: Lippincott Williams &Wilkins; 2007).

2. Non-Arteritic AION (NAION): includes all other cases of AION coincident with cardiovascular risk factors in a patient with "crowded" (i.e., having low cup-to-disc ratio) optic discs. NAION is the most common cause of sudden optic nerve-related vision loss and is responsible for 95% of all cases of AION.

Mechanistically NAION cases can be broadly classified into two groups:

Thrombosis or embolism of the posterior ciliary arteries or their subdivisions—these are rare events in NAION;

Transient poor circulation or no circulation in the blood vessels of the optic nerve head is the most common cause of NAION (Hayreh S S. Ischemic optic neuropathy. Prog Retin Eye Res. 2009, 28(1):34-62). Transiently poor circulation or loss of circulation in the optic nerve head can occur due to a transient drop in blood pressure which, in susceptible persons, can result in NAION. In this etiology of AION, there is no actual blockage of the posterior ciliary arteries. A drop in local blood pressure in the capillaries of the optic nerve head also may be caused either by blockage or severe narrowing of the internal carotid artery and/or the ophthalmic artery, or by a rise in intraocular pressure, or some combination of these factors. The severity of damage to the optic nerve head depends on the extent and duration of the resulting ischemia, but is usually less extensive and less severe than damage caused by thrombosis or embolism.

NAION typically presents as an abrupt, painless monoocular vision loss, though a few patients do experience some discomfort. Visual loss varies widely, ranging from minor loss of visual acuity to complete blindness. The deterioration of vision is usually discovered upon waking in the morning. (Hayreh et al., Nonarteritic anterior ischemic optic neuropathy: time of onset of visual loss. Am J Ophthalmol. 1997, 124(5):641-7).

Visual field defects in NAION are characteristic with patients typically complaining of loss of vision towards the nose and, less commonly, altitudinal loss. Later on, photophobia is a common complaint, particularly in the rare bilateral cases. The optic nerve head acutely appears edematous, which confirms the anterior nature of this disorder. Hemorrhage on the disc is commonly present.

The estimated mean annual incidence of NAION among persons 50 or older ranged from 2.30 to 10.2 per 100,000, (Johnson L N, Arnold A C. Incidence of nonarteritic and arteritic anterior ischemic optic neuropathy. Population-based study in the state of Missouri and Los Angeles County, California. J Neuroophthalmol. 1994, 14(1):38-44) and many sources quote the incidence of NAION as about 8,000/year in the US (Hattenhauer et al., Incidence of nonarteritic anterior ischemic optic neuropathy. Am J Ophthalmol. 1997, 123(1):103-7). NAION is primarily a disease of the middle-aged and elderly, although persons at all ages are at risk. It is more prevalent in men and in the white population relative to other racial groups. Currently there are no approved therapies for NAION.

The neuronal degeneration process can be described in three steps: primary axon damage, concomitant retrograde death of the associated neuronal cell bodies, and subsequent damage/death of adjacent neurons in a process called "secondary degeneration". This secondary degeneration occurs in neurons that initially were not damaged but become exposed to cytokines released during the death of adjacent neurons that experienced primary axonal damage. Both primary retrograde cell death following axonal damage and secondary degeneration are believed to be mediated primarily by apoptosis, or programmed cell death. Accordingly, therapeutic intervention in the form of inhibiting apoptosis could be effective in protecting neurons following primary axonal damage, and those that are lost as a result of secondary degeneration. This strategy may be useful even when the initial cause of the disease is not known because it aims at limiting or preventing neuronal damage/death by blocking the underlying cellular mechanism (apoptosis) that gives rise to optic nerve atrophy. (Brao-Osuna et al., New therapeutic systems of neuroprotectors agents in the treatment of glaucoma. Arch Soc Esp Oftalmol. 2007, 82(4): 191-3).

Direct damage to the ganglion cell body that occurs, for example, during occlusion of the central artery of the retina, leads to rapid death of the nerve in as short as twenty minutes, which is why is it is such a catastrophic disease. In contrast, the site of injury in axogenic diseases like NAION is the axon, where the process of retrograde cell death is much slower.

Optic nerve atrophy is defined as the loss of the fibers of the optic nerve, and results from the death of retinal ganglion cells (RGCs). Since they are unable to divide, loss of RGCs results in irreversible loss of vision. Therefore, therapeutic intervention in diseases that lead to optic nerve atrophy with neuroprotective agents could preserve RGCs and thereby preserve vision.

The majority of the cases of glaucoma are the form known as primary-open-angle glaucoma POAG, also called chronic open-angle glaucoma. POAG results from a build up of aqueous humor fluid within the anterior chamber of the eye resulting in intraocular pressure (IOP). Elevated IOP, which can be measured by a "tonometry" test, results from fluid entering the eye and not enough fluid exiting the eye. Normally, fluid enters the eye by seeping out of the blood vessels in the ciliary body. This fluid eventually makes its way past the crystalline lens, through the pupil (the central opening in the iris), and into the irido-corneal angle, the anatomical angle formed where the iris and the cornea come together. Then the fluid passes through the trabecular meshwork in the angle and leaves the eye via the canal of Schlemm.

If excess fluid enters the eye, or if the trabecular meshwork "drain" gets clogged up (for instance, with debris or cells) so that not enough fluid is leaving the eye, the pressure builds up in what is known as "open angle glaucoma." Open angle glaucoma also can be caused when the posterior portion of the iris adheres to the anterior surface of the lens creating a "pupillary block", and preventing intraocular fluid from passing through the pupil into the anterior chamber.

If the angle between the iris and the cornea is too narrow or is even closed, then the fluid backs up, causing increased pressure in what is known as "closed angle glaucoma."

Acute angle closure glaucoma (AACG) (also called narrow angle glaucoma) is an ocular emergency with acute presentation, need for immediate treatment, and well-established anatomic pathology. AACG is defined as at least two of the following symptoms: ocular pain, nausea/vomiting and a history of intermittent blurring of vision with halos; and at least three of the following signs: IOP greater than 21 mm Hg, conjunctival injection, corneal epithelial edema, mid-dilated nonreactive pupil and shallower chamber in the presence of occlusion.

Primary angle closure glaucoma (PACG) is defined as an occludable drainage angle and features indicating that trabecular obstruction by the peripheral iris has occurred with the presence of glaucomatous optic neuropathy.

Untreated glaucoma eventually leads to optic atrophy and blindness.

CASP2 Double-Stranded RNA (dsRNA) QPI-1007

The CASP2 dsRNA QPI-1007 or the sodium salt thereof is a double-stranded (19-base pair duplex), chemically modified, synthetic RNA targeting Caspase 2 mRNA, for example, the mRNA coding sequence (SEQ ID NO:3-5) for human CASP2, and has the following double-stranded structure:

```
                                  (sense strand; SEQ ID NO: 1)
        5' iB - GCCAGAAUGUGGAACUCCU 3'

(antisense strand; SEQ ID NO: 2)
        3' CGGUCUUACACCUUGAGGA 5'
``` wherein each A, C, U, and G is a nucleotide and each consecutive nucleotide is joined to the next nucleotide by a phosphodiester bond;

wherein the sense strand comprises, counting from the 5' terminus, an unmodified ribonucleotide at positions 1, 2, 3, 4, 5, 6, 7, 8, 9, 10, 11, 12, 13, 14, 15, 16, 17 and 19, a L-deoxycytidine at position 18, and an inverted deoxyabasic 5' cap (iB); and wherein the antisense strand comprises, counting from the 5' terminus, a 2'-O-Methyl sugar modified ribonucleotide at positions 2, 4, 6, 8, 11, 13, 15, 17 and 19 and an unmodified ribonucleotide at positions 1, 3, 5, 7, 9, 10, 12, 14, 16 and 18.

The 5' end of the sense strand of QPI-1007 includes an inverted abasic deoxyribose sugar that, in addition to conferring resistance to nuclease degradation, also blocks the ability of the 5' end of the sense strand to be phosphorylated. Without wishing to be bound to theory, this modification prevents RNAi-mediated activity of the sense strand. In addition, an L-DNA moiety was incorporated at position 18 of the sense strand to introduce thermodynamic instability in the duplex to favor loading of the antisense strand into RISC. Without wishing to be bound to theory, only the antisense strand of QPI-1007 is capable of eliciting RNAi activity. The antisense strand of QPI-1007 contains multiple 2'-O Methyl (2'-OMe) sugar modified nucleosides at positions 2, 4, 6, 8, 11, 13, 15, 17 and 19 that confer nuclease resistance to the antisense strand and that attenuates potential seed region-mediated off-target activity, thereby improving the specificity of QPI-1007 to its intended target, caspase 2 mRNA (Jackson et al., Position specific chemical modification of siRNAs reduces "off-target" transcript silencing. RNA. 2006, 12(7):1197-205).

Without wishing to be bound to theory, these chemical modifications confer nuclease resistance and mitigate potential off-target activity that might arise from unwanted RNAi activity elicited by either the sense strand or the seed region of the antisense strand.

Function of Caspase 2

The caspases are a family of cysteine protcases that play a major role in apoptosis, or programmed cell death. Twelve human caspases have been identified and all initially exist in an inactive (zymogen) state, called procaspases (Logue and Martin, Caspase activation cascades in apoptosis. Biochem Soc Trans. 2008, 36(Pt 1):1-9). External stress or death signals, or significant intracellular damage, can trigger apoptosis and subsequent activation of the caspase pathways (Fan et al., Caspase family proteases and apoptosis. Acta Biochim Biophys Sin (Shanghai). 2005, 37(11):719-27). There are two primary classes of caspases in the apoptotic cascade, initiators/activators and executioners. Initiators cleave executioner caspases to their active forms or cleave other proteins in the apoptotic cascade, which subsequently results in executioner caspase activation. The activated executioners continue the apoptotic cascade (Logue and Martin, 2008, op. cit; Kumar S. Caspase function in programmed cell death. Cell Death Differ. 2007, 14(1):32-43). Caspase 2 was one of the first caspases identified, but its role and place in the apoptotic cascade is still debated (Logue, 2008, ibid.; Troy C M, Shelanski M L. Caspase-2 redox. Cell Death Differ. 2003, 10(1):101-7). Structurally, caspase 2 can be classified as an initiator although it has been suggested to have both initiator and executioner activity in neurons (Fan et al., 2005, ibid; Kumar S. Caspase function in programmed cell death. Cell Death Differ. 2007, 14(1):32-43; Troy and Shelanski, 2003, ibid).

Activation of Caspase 2 in Retinal Ganglion Cells

In NAION, RGC damage begins with the axon rather than the cell body (Levin, 2007 op. cit), and cell death can be prolonged (i.e., over several days (Slater et al., Rodent anterior ischemic optic neuropathy (rAION) induces regional retinal ganglion cell apoptosis with a unique temporal pattern. Invest Ophthalmol Vis Sci. 2008, 49(8):3671-6). RGC death in an ischemic event such as NAION is primarily through apoptosis (Katai N, Yoshimura N. Apoptotic retinal neuronal death by ischemia-reperfusion is executed by two distinct caspase family proteases. Invest Ophthalmol Vis Sci. 1999, 40(11):2697-705; Lam et al., Apoptosis and caspases after ischemia-reperfusion injury in rat retina. Invest Ophthalmol Vis Sci. 1999, 40(5):967-75; Singh et al., Cell-specific caspase expression by different neuronal phenotypes in transient retinal ischemia. J Neurochem. 2001, 77(2):466-75). The caspases play a major role in apoptosis, and Caspase 2 was shown to be activated specifically in RGCs in rat models of retinal ischemic insult (Singh et al., 2001, ibid; Kurokawa et al., BDNF diminishes caspase-2 but not c-Jun immunoreactivity of neurons in retinal ganglion cell layer after transient ischemia. Invest Ophthalmol Vis Sci. 1999, 40(12):3006-11). In the rat model of transient global retinal ischemia, IVT administration of a pan-caspase inhibitor (Lam et al., 1999, ibid) or a Caspase 2-specific inhibitor (Singh et al., 2001, ibid) resulted in attenuated retinal damage.

RNA Interference Pathway

RNAi is a ubiquitous pathway present in plants and animals and is thought to have evolved as a defense against viral infection. Often, viruses generate long double-stranded RNAs during replication. Long double-stranded RNAs are not a natural component of eukaryotic cells. A riboendonuclease called "DICER" recognizes and cleaves long double-stranded RNA into discrete 19-21 base pair double-stranded RNA products called small interfering RNAs (siRNAs). An enzyme complex called the RNA-induced silencing complex (RISC) utilizes the fragments generated by DICER as guide sequences to seek out and cleave RNAs matching the loaded siRNA, thereby distinguishing exogenous viral RNAs from self RNA.

Synthetic siRNAs

Manipulation of the RNAi pathway to inhibit expression of endogenous genes was first demonstrated by Fire and Mello in *C. elegans* using long double-stranded RNA triggers that matched endogenous genes (Fire et al., Potent and specific genetic interference by double-stranded RNA in *Caenorhabditis elegans*. Nature. 1998, 391(6669):806-11). Such long double-stranded RNAs were processed in these forms by DICER into siRNAs, leading to silencing of the targeted genes. However, use of this powerful technique in mammals was hampered because long double-stranded RNAs induce a potent innate immune response leading to induction of the interferon pathway (Robbins et al., siRNA and innate immunity. Oligonucl. 2009, 19(2):89-102).

Elbashir et al., (RNA interference is mediated by 21- and 22-nucleotide RNAs. Genes Dev. 2001, 15(2):188-200) produced 21-nucleotide synthetic siRNA duplexes matching endogenous mammalian genes and demonstrated that such synthetic siRNAs efficiently loaded into RISC (thereby bypassing DICER processing) leading to RNAi-mediated gene silencing in human cells, and that these small synthetic oligonucleotides did not initiate a strong interferon response as seen previously with longer double-stranded RNAs. However, more recent work has shown that some synthetic siRNAs can activate components of the innate immune system, specifically Toll-like Receptor 3 (Kleinman, et al., Sequence- and target-independent angiogenesis suppression by siRNA via TLR3. Nature. 2008, 452(7187):591-7). Chemical modification of one or both of the RNA strands can attenuate, or even abrogate, immune system activation.

Pharmacology of QPI-1007

The pharmacology program for QPI-1007 included in vitro studies which demonstrated RNAi-mediated reduction of Caspase 2 mRNA, cleavage of Caspase 2 mRNa (shown by RACE) and reduced potential for off-target activity; and animal studies which demonstrated i) uptake of fluorescent-labeled siRNA in RGCs following intravitreal (IVT) administration, ii) RNAi-mediated mechanism of action of QPI-1007 in ocular tissues harvested after IVT administration, iii) efficacy of QPI-1007 in three animal models: a rat ocular hypertension model of glaucoma, and two models of retrograde RGC cell death that are characteristic of RGC death in NAION, the optic nerve axotomy and optic nerve crush models.

RNAi activity of QPI-1007 was assessed in vitro following transfection of QPI-1007 siRNA at various concentrations into human (HeLa) and rat (PC12) cells. Dose-dependent reduction of Caspase 2 mRNA levels was observed in both cell types. The potential of QPI-1007 to inhibit unintended targets was evaluated in a cell culture system. Data demonstrate that the potential for QPI-1007 to elicit substantial off-target effects is low.

In the rat axotomy and optic nerve crush (ONC) models of retrograde RGC cell death, IVT administration of siRNA resulted in significant protection of RGCs. In the rat axotomy model, two 10 µg/eye (10 microgram/eye) IVT administrations of CASP2 siRNA more than doubled the RGC survival rate two weeks post-axotomy. IVT administration of QPI-1007 in the rat ONC model led to dose-dependent protection of RGCs, with complete preservation of RGCs 7 days post-injury at doses of 20 and 35 µg/eye. In the rat intraocular hypertension model of glaucoma, a single 20 µg/eye IVT administration of QPI-1007 two weeks following induction of increased intraocular pressure afforded significant protection of RGCs.

Overall, the nonclinical pharmacology studies provide evidence of the pharmacological activity of QPI-1007 in a variety of in vitro and in vivo systems. Taken together, these data support the clinical development of QPI-1007 as a neuroprotectant for the treatment of ocular diseases, disorders and injury, such as nonarteritic anterior ischemic optic neuropathy and other optic neuropathies that result in the death of retinal ganglion cells.

Pharmaceutical Compositions, Kits, and Containers

Provided herein are compositions, kits, containers and formulations that include the double-stranded RNA compound provided herein for administering to a patient, preferably to a patient's eye.

In certain embodiments, the composition is administered in combination with an anesthetic. In some embodiments, the anesthetic is a topical anesthetic suitable for administration to the human eye.

In certain embodiments, the composition is administered in combination with a broad-spectrum microbiocide. In some embodiments the broad-spectrum microbiocide is a broad-spectrum topical microbiocide. In various embodiments, the broad-spectrum topical microbiocide.

In certain embodiments, a topical anesthetic and a broad-spectrum topical microbiocide are applied to the eye prior to administration of the composition.

In certain embodiments, the composition is administered in combination with an antibiotic. In various embodiments, the antibiotic is an antibiotic suitable for administration to the eye. In various embodiments, the antibiotic is formulated as eye drops. In certain embodiments, the antibiotic is administered to the patient following the administration of the composition.

In certain embodiment, the composition further comprises a broad-spectrum microbiocide, an antibiotic or a combination thereof.

As provided herein, a kit may include at least one container and at least one label. Suitable containers include, for example, bottles, vials, syringes, and test tubes. The containers can be formed from a variety of materials such as glass, metal or plastic. The container can hold the compound. The container can alternatively hold a composition comprising the compound.

A kit may further include a second container that includes a pharmaceutically acceptable buffer, such as phosphate-buffered saline, Ringer's solution and/or dextrose solution. It can further include other materials desirable from a commercial and user standpoint, including other buffers, diluents, filters, stirrers, needles, syringes, and/or package inserts with indications and/or instructions for use.

The unit dosage ampoules or multidose containers, in which the compound is packaged prior to use, may include an hermetically sealed container enclosing an amount of the compound suitable for a pharmaceutically effective dose thereof, or multiples of an effective dose. The compound is packaged as a sterile formulation, and the hermetically sealed container is designed to preserve sterility of the formulation until use.

The container which includes the compound may further include a package that is labeled, and the label may bear a notice in the form prescribed by a governmental agency, for example the Food and Drug Administration, which notice is reflective of approval by the agency under Federal law, of the manufacture, use, or sale of the compound therein for human administration.

Federal law requires that the use of pharmaceutical compositions in the therapy of humans be approved by an agency of the Federal government. In the United States, enforcement is the responsibility of the Food and Drug Administration, which issues appropriate regulations for securing such approval, detailed in 21 U.S.C. section 301-392. Similar approval is required by most foreign countries. Regulations vary from country to country, but individual procedures are well known to those in the art and the compositions and methods provided herein preferably comply accordingly.

EXAMPLES

Without further elaboration, it is believed that one skilled in the art can, using the preceding description, utilize the present invention to its fullest extent. The following preferred specific embodiments are, therefore, to be construed as merely illustrative, and not limitative of the claimed invention in any way.

Example 1: Test Compound

The test compound QPI-1007 is a sodium salt of a double-stranded RNA compound having the structure:

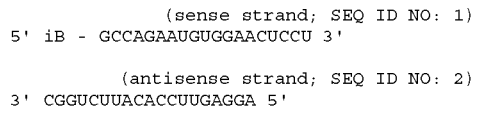

wherein each A, C, U, and G is a nucleotide and each consecutive nucleotide is joined to the next nucleotide by a phosphodiester bond;

wherein the sense strand comprises, counting from the 5' terminus, an unmodified ribonucleotide at positions 1, 2, 3, 4, 5, 6, 7, 8, 9, 10, 11, 12, 13, 14, 15, 16, 17 and 19, a L-deoxycytidine at position 18, and an inverted deoxyabasic 5' cap; and wherein the antisense strand comprises, counting from the 5' terminus, a 2'-O-Me (2'-O-Methyl, 2' methoxy) sugar modified ribonucleotide at positions 2, 4, 6, 8, 11, 13, 15, 17 and 19 and an unmodified ribonucleotide at positions 1, 3, 5, 7, 9, 10, 12, 14, 16 and 18;

The Molecular Formula of QPI-1007 Sodium Salt is: C(375) H(439) N(143) Na(37) O(266) P(37).

The Molecular Weight of QPI-1007 Sodium Salt is: 13,202 Da.

Example 2: First in Human Open Label Phase I Clinical Trial of QPI-1007 in NAION Patients The study was designed to enroll up to 66 patients in two separate strata as described below.

Dosing of the first cohort of Stratum I commenced at the first dose level of 0.2 mg in a single eye and subsequent Stratum I cohorts were recruited sequentially to receive escalating doses of QPI-1007 (FIG. 1). In this stratum, no more than one patient received QPI-1007 in any 24-hour period.

Following administration of QPI-1007 to the last patient in a cohort in Stratum I, a 7-day follow-up period and a review of available safety data is required before the first patient in the next cohort receives QP1-1007.

Figure 2:
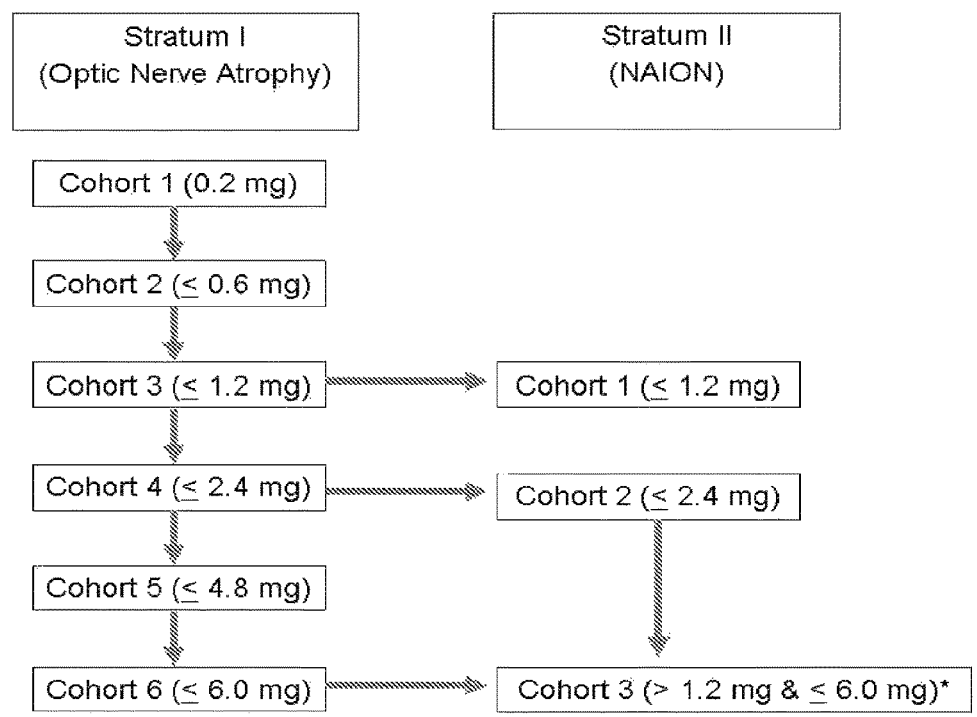
FIG. 2 provides a flow chart outlining the Dose Escalation program

FIG. 2 provides a flow chart outlining the Dose Escalation program.

Inclusion Criteria: Patients meet the following inclusion criteria:

Stratum I

1. "Legally blind" in the study eye using the US definition of visual acuity of less than or equal to 20/200 or visual field restricted to less than 20 degrees. This level of visual function must have been stable for a minimum of 6 months prior to screening. Stable is defined as the same visual acuity score at screening and at least 6 months previously using the same visual acuity test (ETDRS or Snellen).

2. Blindness is the result of an irreversible condition affecting the posterior segment of the study eye. These conditions include, but are not limited to: Retinal degeneration, Optic neuritis End stage glaucoma, Optic nerve atrophy due to any etiology, Leber's hereditary optic neuropathy with onset at least 2 years prior to screening.

3. Clear ocular media and able to undergo adequate pupil dilation to allow a good fundus examination.

4. Both visual acuity and visual field in the non-study eye are better than or equal to the study eye at screening.

Stratum II

1. Positive diagnosis of NAION with symptom onset within 14 days prior to planned dosing with QPI-1007.

The NAION diagnosis required all of the following: Disc edema, Visual field defects in the study eye consistent with optic neuropathy and mean deviation on Humphrey SITA standard 24-2 worse than −3.0 dB, Relative afferent pupillary defect (if the study eye is the first eye affected).

2. Best-corrected visual acuity in the study eye is worse than or equal to 20/64 and better than or equal to light perception.

3. Best corrected visual acuity and visual field in the non-study eye are better than or equal to the study eye at screening.

Test Product, Dose, and Mode of Administration:

Test Product: The active pharmaceutical ingredient of QPI-1007 is a sodium salt of a double-stranded (19-base pair), chemically modified, synthetic siRNA targeting Caspasc 2 mRNA. QPI-1007 has been manufactured in accordance with Good Manufacturing Practices (GMP).

The drug product, "QPI-1007 Injection", is a preservative-free, sterile solution formulated at 60 mg/mL in phosphate-buffered saline. QPI-1007 was supplied as a sterile solution for IVT injection in a 2 mL Type I glass vials sealed with Teflon-coated butyl rubber stoppers with aluminum flip-off overseals. Each vial was intended for single use and contains volume sufficient to dose concentrations defined by the protocol. QPI-1007 was diluted to the target concentration with an appropriate volume of diluent. The final concentration to be prepared was determined by the intended dose level.

QPI-1007 Injection was stored refrigerated at 2-8° C., protected from light. The solution was warmed to room temperature prior to use.

Mode of Administration

In the study, QPI-1007 was administered via intravitreal (IVT) injection. QPI-1007 was diluted with a sterile saline solution suitable for injection into the eye to achieve the correct concentration to be delivered by IVT injection.

Preparation for administration was done using aseptic techniques. The IVT injection procedure was carried out under controlled aseptic conditions, which included the use of sterile gloves, a sterile drape, and a sterile eyelid speculum (or equivalent). Adequate topical anesthetic and a broad-spectrum topical microbiocide were given prior to the injection.

Following the IVT injection, patients were monitored for elevation of intraocular pressure, decreased optic nerve head perfusion and for possible injection complications (vitreous hemorrhage, retinal tears). Additionally, patients had to report any symptoms suggestive of endophthalmitis, such as ocular pain, swelling, redness, haze and gradual loss of vision immediately.

Patients were prescribed antibiotic eye drops following administration of QPI-1007.

Detailed guidelines on IVT injection procedures are known in the art (Aiello, et al., Evolving guidelines for intravitreous injections. Retina. 2004, 24(5 Suppl):S3-19; Brucker (Brucker A J. Maximizing the Safety of Intravitreal Injections. Medscape Ophthalmology [Internet]. 2006 7(2)).

Dosing

Stratum I: QPI-1007 was administered as a single IVT injection to patients in each cohort according to the following schedule in Table 1.

TABLE 1

| Cohort | N patients | Dose per Injection (mg) |
| --- | --- | --- |
| 1 | 3 to 6 | 0.2 |
| 2 | 3 to 6 | Up to 0.6 |
| 3 | 3 to 6 | Up to 1.2 |
| 4 | 3 to 6 | Up to 2.4 |
| 5 | 3 to 6 | Up to 4.8 |
| 6 | 3 to 6 | Up to 6.0 |

Stratum II: QPI-1007 was administered as a single IVT injection to patients in each cohort according to the following schedule in Table 2.

TABLE 2

| Cohort | N Patients | Dose per Injection (mg) |
| --- | --- | --- |
| 1 (following Stratum I, Cohort 3) | Up to 10 | Up to 1.2 |
| 2 (following Stratum I, Cohort 4) | Up to 10 | Up to 2.4 |
| 3 (following Stratum I & II, Cohorts 1 & 2) | Up to 10 | >1.2 and ≤6.0 |

Duration of Treatment and Follow-Up:

Stratum I

In Stratum I all screening procedures were performed within 28 days prior to IVT injection of QPI-1007 (on Study Day 0).

At screening, patients underwent an ophthalmic evaluation (both eyes) including best corrected visual acuity (BCVA) assessment, visual field assessment, tonometry, slit lamp examination of the anterior segment and slit lamp/ophthalmoscope examination of the posterior segment, fundus photography (FP), and optical coherence tomography (OCT) of the macula and of the peripapillary retinal nerve fiber layer.

Prior to IVT injection of QPI-1007 on Study Day 0, the patient underwent a BCVA assessment and tonometry in both eyes. 30 minutes following IVT injection the patient's study eye was examined by tonometry to determine intraocular pressure, and by slit-lamp/ophthalmoscope to determine the status of optic nerve perfusion and to check for any retinal hemorrhage or tears. Patients were monitored in the clinic for 4 hours following injection as per the schedule of events. Patients returned to the clinic the day following IVT injection (Study Day 1) for a safety assessment of both eyes including BCVA assessment, tonometry, slit lamp examination of the anterior segment and slit lamp/ophthalmoscope examination of the posterior segment.

On Study Days 7, 14 and 28 and at Study Weeks 8 and 12 after IVT injection of QPI-1007, patients underwent an ophthalmic evaluation (both eyes) including BCVA assessment, tonometry and slit lamp examination of the anterior segment and slit lamp/ophthalmoscope examination of the posterior segment. In addition, patients underwent a visual field assessment, FP and OCT of the macula and of the peripapillary retinal nerve fiber layer at Study Week 12 only.

Follow-up visits occur at Study Months 6 and 12 after IVT injection of QPI-1007. Patients underwent an ophthalmic evaluation (both eyes) including BCVA assessment, tonometry and slit lamp examination of the anterior segment and slit lamp/ophthalmoscope examination of the posterior segment.

Patient safety was monitored during the study by evaluation of vital signs, clinical laboratory testing, physical examinations, collection of adverse events (AEs) and review of concomitant medications.

Stratum II

In Stratum II, all screening procedures were performed within 48 hours prior to IVT injection of QPI-1007 (on Study Day 0), and were conducted on the same day as the IVT injection. Patients received the QPI-1007 injection no more than 14 days from the onset of NAION symptoms.

At screening, patients underwent an ophthalmic evaluation (both eyes) including BCVA assessment, visual field assessment, tonometry, slit lamp examination of the anterior segment and slit lamp/ophthalmoscope examination of the posterior segment, FP and OCT of the macula and of the peripapillary retinal nerve fiber layer.

Prior to IVT injection of QPI-1007 on Study Day 0, the patient underwent tonometry (both eyes). 30 minutes following IVT injection, the patient's study eye was examined by tonometry to determine intraocular pressure and by slit-lamp/ophthalmoscope to determine the status of optic nerve perfusion and to check for any retinal hemorrhage or tears. Patients were monitored in the clinic for 4 hours following IVT injection as per the schedule of events. Patients returned to the clinic the next day following IVT injection (Study Day 1) for a safety assessment of both eyes including BCVA assessment, tonometry, slit lamp examination of the anterior segment and slit lamp/ophthalmoscope examination of the posterior segment.

On Study Days 7, 14 and 28 and at Study Weeks 8 and 12 after IVT injection of QPI-1007, patients underwent an ophthalmic evaluation (both eyes) including BCVA assessment, tonometry, slit lamp examination of the anterior segment and slit lamp/ophthalmoscope examination of the posterior segment, FP and OCT of the macula and of the peripapillary retinal nerve fiber layer. In addition, on Study Days 7 and 28 and at Study Week 12, patients underwent a visual field assessment.

Follow-up visits occur at Study Months 6 and 12 after IVT injection of QPI-1007. Patients underwent an ophthalmic evaluation (both eyes) including BCVA assessment, tonometry, slit lamp examination of the anterior segment and slit lamp/ophthalmoscope examination of the posterior segment, FP and OCT of the macula and of the peripapillary retinal nerve fiber layer. In addition, at Study Month 6 only, patients received a visual field assessment.

Patient safety was monitored on an ongoing basis during the study including but not limited to study assessments including evaluation of vital signs, clinical laboratory testing, physical examinations, collection of AEs and review of concomitant medications.

Ophthalmic Evaluations

The following ophthalmic evaluations were performed for both eyes for patients enrolled in Stratum 1:

Best Corrected Visual Acuity (BCVA) was assessed using the ETDRS chart starting at 4 meters at Screening and on Study Days 0 (pre-injection, if Screening assessment was conducted more than 48 hours previously), 1, 7, 14 and 28, Study Weeks 8 and 12/ET and Study Months 6 and 12.

Visual field was assessed using the SITA Standard algorithm at Screening and Study Week 12/ET.

Slit lamp examination of the anterior segment of the eye was performed without pupillary dilation, whenever possible. Any abnormalities of the anterior chamber, eyelids, conjunctivae, iris, lens and cornea were documented at Screening and on Study Days 1, 7, 14 and 28, Study Weeks 8 and 12/ET and Study Months 6 and 12. Any anterior chamber inflammation, phakic status and posterior lens capsule status were noted.

Intraocular pressure (IOP) was measured using Goldmann applanation tonometry at Screening and on Study Days 0 (pre-injection), 1, 7, 14 and 28, Study Weeks 8 and 12/ET and Study Months 6 and 12. Whenever possible, tonometry was performed prior to pupillary dilation.

Slit lamp/ophthalmoscope examination of the posterior segment of the eye was performed after pupillary dilation to examine the vitreous body, optic nerve head, macular and peripheral retina and fundus at Screening and on Study Days 1, 7, 14 and 28, Study Weeks 8 and 12/ET and Study Months 6 and 12. Any vitreous inflammation was noted.

Fundus photographs were obtained at Screening and Study Week 12/ET only.

Optical coherence tomography of the macula and of the peripapillary retinal nerve fiber layer was obtained at Screening and Study Week 12/ET only.

In addition, the following ophthalmic evaluations were performed in the study eye only 30 minutes post-injection on Study Day 0 for patients enrolled in Stratum I: Slit lamp examination of the anterior segment, Slit lamp/ophthalmoscope examination of the posterior segment, IOP measured by Goldmann applanation tonometry.

The following ophthalmic evaluations were performed for both eyes for patients enrolled in Stratum II:

Best Corrected Visual Acuity (BCVA) was assessed using the ETDRS chart starting at 4 meters at Screening and on Study Days 1, 7, 14 and 28, Study Weeks 8 and 12/ET and Study Months 6 and 12.

Visual field was assessed at Screening, Study Days 7 and 28, Study Week 12/ET, and Study Month 6.

Slit lamp examination of the anterior segment of the eye was performed without pupillary dilation, whenever possible. Any abnormalities of the anterior chamber, eyelids, conjunctivae, iris, lens and cornea were documented at Screening and on Study Days 1, 7, 14 and 28, Study Weeks 8 and 12/ET and Study Months 6 and 12. Any anterior chamber inflammation, phakic status and posterior lens capsule status were noted.

Intraocular pressure (TOP) was measured using Goldmann applanation tonometry at Screening and on Study Days 0 (pre-injection), 1, 7, 14 and 28, Study Weeks 8 and 12/ET and Study Months 6 and 12. Whenever possible, tonometry was performed prior to pupillary dilation.

Slit lamp/ophthalmoscope examination of the posterior segment of the eye was performed after pupillary dilation to examine the vitreous body, optic nerve head, macular and peripheral retina and fundus at Screening and on Study Days 1, 7, 14 and 28, Study Weeks 8 and 12/ET and Study Months 6 and 12. Any vitreous inflammation was noted.

Fundus photographs were obtained at Screening and on Study Days 7, 14, and 28, Study Weeks 8 and 12/ET, and are obtained at Study Months 6 and 12.

Optical coherence tomography of the macula and of the peripapillary retinal nerve fiber layer was obtained at Screening and on Study Days 7, 14, and 28, Study Weeks 8 and 12/ET, and are obtained at Study Months 6 and 12.

In addition, the following ophthalmic evaluations were performed in the study eye only 30 minutes post-injection on Study Day 0 for patients enrolled in Stratum II: Slit lamp examination of the anterior segment, Slit lamp/ophthalmoscope examination of the posterior segment, TOP measured using Goldmann applanation tonometry.

TABLE 3

QPI-1007 Study Schedule - Stratum I - Optic Nerve Atrophy Patients

| Procedures | Screening (≤28 days of Injection) | Active Study Period Study Visits | | | | | | | Follow up month 6 | Follow up month 12 |
|---|---|---|---|---|---|---|---|---|---|---|
| | | Day 0 | Day 1 | Day 7 | Day 14 | Day 28 | Week 8 | Week 12/ET | | |
| Written Informed Consent | X | | | | | | | | | |
| Demographics | X | | | | | | | | | |
| Physical Exam | X | | | | | | | X | | |
| Medical History | X | | | | | | | | | |
| Medication History | X | | | | | | | | | |
| Clinical Labs | X | | | | | | | X | | |
| Pregnancy Test | X | X[1] | | | | | | X | | |
| Assess Eligibility Criteria | X | X | | | | | | | | |
| Administer QPI-1007 | | X | | | | | | | | |
| Vital Signs | X | X[2] | X | X | X | X | X | X | | |
| BCVA | X | X[1] | X | X | X | X | X | X | X | X |
| Visual Field | X | | | | | | | X | | |
| Slit lamp exam (anter. segment) | X | X[3] | X | X | X | X | X | X | X | X |
| IOP/Goldmann Applanation Tonometry | X | X[4] | X | X | X | X | X | X | X | X |
| Slit lamp/ ophthalmoscope exam (post segment) | X | X[3] | X | X | X | X | X | X | X | X |
| Fundus photography | X | | | | | | | X | | |
| OCT | X | | | | | | | X | | |
| PK Blood draw[7] | | X[5] | X[6] | X | X | | | | | |
| Concomitant Medications | | X | X | X | X | X | X | X | | |
| All AEs | | X | X | X | X | X | X | X | | |
| Ocular AEs of special interest only | | | | | | | | | X | X |

[1]Pre-injection only - do not repeat if screening was conducted within 48 hours of QPI-1007 injection
[2]Pre-injection, 30 minutes and 4 hours post-injection
[3]30 minutes post-injection (study eye only)
[4]Pre-injection (both eyes) and 30 minutes post-injection (study eye only)
[5]Pre-injection, 1 and 4 hours post-injection
[6]24 hours post-injection
[7]For the first 3 patients of every cohort only

TABLE 4

QPI-1007 Study Schedule - Stratum II- NAION Patients

| Procedures | Screening[1] (≤48 days of Injection) | Active Study Period Study Visits | | | | | | | Follow up month 6 | Follow up month 12 |
|---|---|---|---|---|---|---|---|---|---|---|
| | | Day 0 | Day 1 | Day 7 | Day 14 | Day 28 | Week 8 | Week 12/ET | | |
| Written Informed Consent | X | | | | | | | | | |
| Demographics | X | | | | | | | | | |
| Physical Exam | X | | | | | | | X | | |
| Medical History | X | | | | | | | | | |
| Medication History | X | | | | | | | | | |
| Clinical Labs | X | | | | | | | X | | |
| Pregnancy Test | X | | | | | | | X | | |
| Assess Eligibility Criteria | X | | | | | | | | | |
| Administer QPI-1007 | | X | | | | | | | | |
| Vital Signs | X | X[2] | X | X | X | X | X | X | | |
| BCVA | X | | X | X | X | X | X | X | X | X |
| Visual Field | X | | | X | | X | | X | X | |

TABLE 4-continued

QPI-1007 Study Schedule - Stratum II- NAION Patients

| Procedures | Screening[1] (≤48 days of Injection) | Active Study Period Study Visits | | | | | | Follow up month 6 | Follow up month 12 |
|---|---|---|---|---|---|---|---|---|---|
| | | Day 0 | Day 1 | Day 7 | Day 14 | Day 28 | Week 8 | Week 12/ET | | |
| Slit lamp exam (anter. segment) | X | X[3] | X | X | X | X | X | X | X | X |
| IOP/Goldmann Applanation Tonometry | X | X[4] | X | X | X | X | X | X | X | X |
| Slit lamp/ ophthalmoscope exam (posterior segment) | X | X[3] | X | X | X | X | X | X | X | X |
| Fundus photography | X | | | X | X | X | X | X | X | X |
| OCT | X | | | X | X | X | X | X | X | X |
| PK Blood Draw[7] | | X[5] | X[6] | X | X | | | | | |
| Concomitant Medications | | X | X | X | X | X | X | X | | |
| All AEs | | X | X | X | X | X | X | X | | |
| Ocular AEs of special interest only | | | | | | | | | X | X |

[1]Screening and Study Day 0 may occur on the same day
[2]Pre-injection, 30 minutes and 4 hours post-injection
[3]30 minutes post-injection (study eye only)
[4]Pre-injection (both eyes) and 30 minutes post-injection (study eye only)
[5]Pre-injection, 1 and 4 hours post-injection
[6]24 hours post-injection
[7]For the first 3 patients of every cohort only Results:

Subjects with long-standing low vision due to retinal or optic nerve pathology and subjects with acute NAION were studied in a 1 year, 2-stratum, Phase I, multi-center, open-label, dose escalation study to determine safety, tolerability and the structural and functional changes after a single IVT injection of QP1-1007, a synthetic, chemically modified siRNA that inhibits expression of caspase 2.

Low-vision subjects with visual acuity (VA)≤20/200 (Stratum I) and NAION subjects with ≤20/40 and symptom onset within 28 days prior to the study drug injection (Stratum II-S2) were enrolled in 6 cohorts (0.2-6 mg) and 3 cohorts (1.2, 2.4 and 6 mg), respectively. After receiving a single IVT injection, subjects were evaluated for VA, visual field (VF) and retinal nerve fiber layer (RNFL) thickness at days 1, 7, 14, 28, and months 2, 3, 6, 12.

48 subjects (18 low vision, 30 NAION) were enrolled. All expected study visits are complete for all subjects, except the final follow-up visit (Month 12) for the last enrolled cohort (S2, 6 mg). Available data from both strata through Month 3 (n=48), Month 6 (n=48) and Month 12 (n=38) were analyzed. 261 of 273 adverse events (AEs) were of mild-to-moderate severity. There were no serious AEs. The most common AEs were conjunctival hemorrhage (n=29), conjunctival chemosis (n=11), and eye pain (n=11). Among 28 NAION subjects in S2 with on-chart VA, maximum VA gain was at Month 2 (mean±SD: 16.4±10.4 letters). The proportion of subjects in S2 (FIG. 1) improving by ≥3 lines at Months 3 and 6 were 53.6% (n=15), and 50.0% (n=14) compared with 39.7% (n=48), and 42.6% (n=52) of Ischemic Optic Neuropathy Decompression TrialIONDT) historical controls (p=0.2 and 0.5, respectively; Fisher exact test) [Ischemic Optic Neuropathy Decompression Trial, Arch Ophthalmol. 2000; 118(6):793-797]. Of all the S2 subjects with available follow-up data, no subject lost ≥3 lines of VA compared with 9.1% (n=11), 14.8% (n=18), and 15.8% (n=18) at Months 3, 6 and 12, respectively, in the IONDT historical controls. VF mean defect was comparable to baseline. Decrease in RNFL thickness was similar to historical controls [Contreras et al., 2007].

CONCLUSION

A single IVT injection of QPI-1007 was well tolerated in subjects with long-standing low vision or acute NAION. Patients treated by a single IVT injection of QPI-1007 were protected from further loss of visual acuity compared to published historical data on untreated NAION patients with similar initial disease severity.

Example 3: A Phase II Pivotal Randomized, Double Masked, Sham-Controlled Trial of QPI 1007 Delivered by a Intravitreal Injections to Patients with Acute Non Arteritic Anterior Ischemic Optic Neuropathy (NAION)

Study Design:

This is a double masked, randomized sham-controlled efficacy and safety study. The study will enroll up to 240 patients with an acute NAION. Patients will be randomized into one of 3 groups in a 1:1:1 ratio. Two groups will receive treatment with QPI-1007, and the third group will receive a sham injection.

Patients randomized to one of the treatment groups will receive monthly intravitreal injections of either 2.4 mg or 6.0 mg of QPI-1007 in the study eye on the day of randomization and at study month 1, 2, 3, 4 and 5. Subjects will be stratified by baseline (Day 0) BCVA score (>20/64 and ≤20/64) and by country. Patients randomized to the sham-control arm will receive a sham-injection in the study eye on the day of randomization and study month 1, 2, 3, 4 and 5. Patients, technicians and Investigators will be masked to treatment arm. Only the injecting physician will be unmasked, but will not be involved in patient evaluations other than the immediate post-injection patient evaluation.

Patients will be followed monthly for 6 months, with a final follow up visit at month 12. Study procedures are listed in the Schedule of Events Table below.

Inclusion Criteria:

Patients must meet the following inclusion criteria:

1. Positive diagnosis of Non-Arteritic AION (NAION) with symptom onset within 28 days prior to planned dosing with QPI-1007. The NAION diagnosis requires all of the following: Disc edema, Visual field defects in the study eye consistent with optic neuropathy and mean deviation on Humphrey SITA standard 24-2 worse than −3.0 dB and Relative afferent pupillary defect (if the study eye is the first eye affected)

2. Best-corrected visual acuity score in the study eye is worse than or equal to 20/20 and better than or equal to 20/400 Snellen equivalents, measured on the ETDRS chart 3. 50 years old or older at screening.

4. Clear ocular media and able to undergo adequate pupil dilation to allow a good fundus examination.

5. Capable of giving written informed consent.

6. Willing and able to comply with the study procedures and visit schedule, including follow-up visits.

7. Female patients must be: (1) post-menopausal (2) surgically sterile, or (3) using an effective means of contraception which will be continued until the Study Month 6 visit with a negative pregnancy test within 48 hours prior to administration of QPI-1007. Male patients with female partners of child bearing potential must agree to use an effective means of contraception which will be continued until the Study Month 6 visit. Note: For the purpose of this study, post-menopausal is defined as the absence of menses for at least one year and a serum FSH level ≥20 IU/L. Investigators can determine if a serum FSH level is required to prove post-menopausal status. A woman is considered to be surgically sterilized if she has had a bilateral tubal ligation for at least 6 months prior to administration of QPI-1007, bilateral oophorectomy, or complete hysterectomy. Effective means of contraception include use of one of the following: hormonal contraceptives (oral, implant, transdermal patch, or injection) at a stable dose for at least 3 months prior to administration of QPI-1007, barrier (condom with spermicide, diaphragm with spermicide), IUD, or a male patient/partner who has been vasectomized for at least 6 months prior to administration of QPI-1007.

Test Product, Dose, and Mode of Administration

QPI-1007 is a double-stranded (19-base pair), chemically-modified, synthetic siRNA targeting caspase 2 mRNA and is designed to temporarily inhibit the expression of caspase 2. QPI-1007 will be supplied as a sterile solution for IVT injection in a 2 mL glass vial. The drug product will be diluted to the target concentration with an appropriate volume of diluent. QPI-1007 will be administered as an IVT injection. All IVT injections will be at the same volume of injection (100 µl). There is no reference therapy administered in this study.

Duration of Treatment and Follow-Up

Patients must receive the first QPI-1007 injection no more than 28 days from the onset of NAION symptoms. If both eyes have NAION and are eligible for the study enrollment, the eye with the worse VA will be chosen as the study eye. If both eyes have the same VA, the eye chosen by the patient and agreed by the Investigator will be assigned as the study eye.

At screening, patients will undergo an ophthalmic evaluation (both eyes) including BCVA assessment, visual field assessment, tonometry, slit lamp examination of the anterior segment and slit lamp/ophthalmoscope examination of the posterior segment, fundus photo (FP) and SD-OCT of the macula and of the peripapillary retinal nerve fiber layer.

Prior to IVT injection of QPI-1007, the patient will undergo BCVA assessment and tonometry (both eyes), and a comprehensive anterior and posterior segment eye exam, as detailed in the events table below. Immediately after the IVT injection, the patient's injected eye will be examined for optic nerve head perfusion. Within 30 minutes following IVT injection, the patient's study eye will be examined by tonometry to determine intraocular pressure and by slit-lamp/ophthalmoscope to determine the status of optic nerve perfusion and to check for any retinal hemorrhage or tears. Patients will be monitored in the clinic for up to 4 hours following IVT injection as per the schedule of events.

On Study Days 7, and Study Months 1, 2, 3, 4, 6 and 12, patients will undergo an ophthalmic evaluation (both eyes) including BCVA assessment, tonometry, slit lamp examination of the anterior segment and slit lamp/ophthalmoscope examination of the posterior segment. In addition, on Study Day 0, and Study Months 3, 6 and 12, patients will undergo FP, color vision testing, contrast sensitivity testing and SD-OCT of the macula and of the peripapillary retinal nerve fiber layer. On Study Day 0 and Study Months 6 and 12 patients will undergo a visual field assessment.

SD-OCT and visual field assessments will be sent to a central reading center for evaluation.

Patient safety will be monitored on an ongoing basis during the study including but not limited to study assessments including evaluation of vital signs, clinical laboratory testing, physical examinations, and collection of reported AEs and review of concomitant medications.

TABLE 5

Schedule of Events

| VISIT | Screening 1 | Day 0 2 | Day 7 3 | Month 1 4 | Month 2 5 | Month 3 6 | Month 4 7 | Month 5 8 | Month 6 9 | Month 12 10 |
|---|---|---|---|---|---|---|---|---|---|---|
| Sign Informed Consent | X | | | | | | | | | |
| Demographics | X | | | | | | | | | |
| Medical/Ophthalmic History | X | X | | | | | | | | |
| Physical Exam | X | | | | | | | | | |
| Vital Signs and Weight | X | X | X | X | X | X | X | X | X | X |
| Clinical Labs | X | | | | | | | | X | X |
| Pregnancy test | X | | X | X | X | X | X | X | X | X |
| EKG | X | | | | | | | | X | X |

TABLE 5-continued

Schedule of Events

| VISIT | Screening 1 | Day 0 2 | Day 7 3 | Month 1 4 | Month 2 5 | Month 3 6 | Month 4 7 | Month 5 8 | Month 6 9 | Month 12 10 |
|---|---|---|---|---|---|---|---|---|---|---|
| BCVA (ETDRS) | X | X | X | X | X | X | X | X | X | X |
| RAPD | X | X | X | X | X | X | X | X | X | X |
| Color Vision | X | X | | | | X | | | X | X |
| Contrast sensitivity | X | X | | | | X | | | X | X |
| Visual Field (Humphrey 24-2 protocol) | X | X | | | | | | | X | X |
| Slit lamp exam (anterior segment) | X | X | X | X | X | X | X | X | X | X |
| IOP | X | X | X | X | X | X | X | X | X | X |
| Posterior segment evaluation | X | X | X | X | X | X | X | X | X | X |
| Fundus Photography | | X | | | | X | | | X | X |
| SD-OCT | | X | | | | X | | | X | X |
| IVT 2.4 or 6 or Sham Injection | | X | | X | X | X | X | X | | |
| Post-Injection posterior segment evaluation | | X | | X | X | X | X | X | | |
| Post-Injection IOP | | X | | X | X | X | X | X | | |
| Concomitant medication | X | X | X | X | X | X | X | X | X | X |
| Adverse Events | | X | X | X | X | X | X | X | X | X |

Results: According to the results that are obtained in this study, multiple monthly IVT injections of QPI-1007 are well tolerated in subjects with acute NAION. Patients treated by a multiple monthly IVT injections of QPI-1007 are protected from further loss of visual acuity compared to published historical data on untreated NAION patients with similar initial disease severity.

Although the above examples have illustrated particular ways of carrying out embodiments of the invention, in practice persons skilled in the art will appreciate alternative ways of carrying out embodiments of the invention, which are not shown explicitly herein. It should be understood that the present disclosure is to be considered as an exemplification of the principles of this invention and is not intended to limit the invention to the embodiments illustrated.

Those skilled in the art will recognize, or be able to ascertain using no more than routine experimentation, equivalents of the specific embodiments of the invention described herein. Such equivalents are intended to be encompassed by the following claims.

The invention claimed is:

1. A method of treating a human patient suffering from or at risk for developing any one or more of primary open angle glaucoma (POAG), normal-tension glaucoma, primary angle-closure glaucoma (PACG), acute angle-closure glaucoma (AACG), angle-closure glaucoma, primary angle closure (PAC), or acute angle closure (AAC), the method comprising administering to the patient's eye via intravitreal (IVT) injection a double-stranded ribonucleic acid (dsRNA) compound that down-regulates CASP2 expression, wherein the double-stranded RNA compound has the structure:

```
                              (sense strand; SEQ ID NO: 1)
    5' iB - GCCAGAAUGUGGAACUCCU 3'

(antisense strand; SEQ ID NO: 2)
    3' CGGUCUUACACCUUGAGGA 5'
``` wherein each A, C, U, and G is a nucleotide and each consecutive nucleotide is joined to the next nucleotide by a phosphodiester bond;

wherein each nucleotide is independently an unmodified ribonucleotide, a 2'-O-Methyl sugar modified ribonucleotide, or an L-DNA nucleotide;

wherein the sense strand comprises, counting from the 5' terminus, an unmodified ribonucleotide at each of positions 1, 2, 3, 4, 5, 6, 7, 8, 9, 10, 11, 12, 13, 14, 15, 16, 17, and 19 and a L-deoxycytidine at position 18, and an inverted abasic deoxyribose cap (iB) covalently bound to the 5' terminus;

wherein the antisense strand comprises, counting from the 5' terminus, a 2'-O-Methyl sugar modified ribonucleotide at each of positions 2, 4, 6, 8, 11, 13, 15, 17, and 19 and an unmodified ribonucleotide at each of positions 1, 3, 5, 7, 9, 10, 12, 14, 16, and 18;

or a pharmaceutically acceptable salt thereof; and wherein the compound is administered to the patient's eye at a dose of about 1.2 mg to about 3.0 mg per eye.

2. The method of claim 1, wherein the treatment comprises multiple administrations of the compound.

3. The method of claim 2, wherein the IVT injections are administered six times.

4. The method of claim 2, wherein the multiple administrations occur at regular intervals.

5. The method of claim 2, wherein the compound is administered as six IVT injections at intervals about one month apart.

6. The method of claim 1, wherein the pharmaceutically acceptable salt is a sodium salt.

7. The method of claim 1, wherein the compound is administered to the patient's eye as a liquid composition comprising a pharmaceutically acceptable carrier.

8. The method according to claim 7, wherein a volume of a single dose IVT injection is between about 20 µl to about 200 µl.

9. The method according to claim 7, wherein a volume of a single dose IVT injection is between about 50 µl to about 100 µl.

* * * * *

SEQUENCE LISTING

```
<160> NUMBER OF SEQ ID NOS: 8

<210> SEQ ID NO 1
<211> LENGTH: 19
<212> TYPE: RNA
<213> ORGANISM: Artificial
<220> FEATURE:
<223> OTHER INFORMATION: Chemically synthesized

<400> SEQUENCE: 1
gccagaaugu ggaacuccu                                              19

<210> SEQ ID NO 2
<211> LENGTH: 19
<212> TYPE: RNA
<213> ORGANISM: Artificial
<220> FEATURE:
<223> OTHER INFORMATION: Chemically synthesized

<400> SEQUENCE: 2
aggaguucca cauucuggc                                              19

<210> SEQ ID NO 3
<211> LENGTH: 4242
<212> TYPE: RNA
<213> ORGANISM: Homo_sapiens
<300> PUBLICATION INFORMATION:
<308> DATABASE ACCESSION NUMBER: NM_032982
<309> DATABASE ENTRY DATE: 2012-12-23
<313> RELEVANT RESIDUES IN SEQ ID NO: (1)..(4242)
```

<400> SEQUENCE: 3

```
cuuuugucug uccgccgagc accccacuuc accccauugg accgcgcggc cgccgcuaga        60
gcucugcgcc ugcgcacgca ccgggccggg gacugggugg ccuggugugu gggcgcggca       120
gggcgcaggc gcaggcgcag ugugcguccg cgucugaggg gagggaugug ggggaagcga       180
cggcccccgg uuuguuuggg cuguggcgg ugcgcagcgg agagcccggg aaaagcggga        240
aauggcggcg ccgagcgcgg ggucuugguc caccuuccag cacaaggagc ugauggccgc       300
ugacagggga cgcaggauau ugggagugug uggcaugcau ccucaucauc aggaaacucu       360
aaaaaagaac cgaguggugc uagccaaaca gcuguuguu agcgaauugu uagaacaucu        420
ucuggagaag gacaucauca ccuuggaaau gagggagcuc auccaggcca aguggggcag       480
uuucagccag aauguggaac uccucaacuu gcugccuaag aggggucccc aagcuuuuga       540
ugccuucugu gaagcacuga gggagaccaa gcaaggccac cuggaggaua guugcucac        600
cacccuuucu gggcuucagc auguacuccc accguuagc ugugacuacg acuugagucu        660
cccuuuuccg gugugugagu ccuguccccu uuacaagaag uccgccugu cgacagauac        720
uguggaacac ucccuagaca auaaagaugg uccugucugc cuucagguga agccuugcac       780
uccgaauuu uaucaaacac acuuccagcu ggcauauagg uugcagucuc ggccucgugg        840
ccuagcacug uguuugagca augcacuu cacuggagag aaagaacugg aauuucgcuc         900
uggaggggau guggaccaca guacucuagu caccccucuuc aagcuuuugg gcuaugacgu      960
ccauguucua ugugaccaga cugcacagga aaugcaagag aaacugcaga uuuugcaca      1020
guuaccugca caccgaguca cggacuccug caucgucggca cuccucucgc augguggga    1080
gggcgccauc uauggugugg augggaaacu gcuccagcuc caagagguuu uucagcucuu     1140
ugacaacgcc aacugcccaa gccuacagaa caaaccaaaa auguucuuca ccaggccug     1200
ccguggagau gagacugauc gugggguuga ccaacaagau ggaagaaccu acgcaggauc   1260
cccugggugc gaggagagug augccgguaa gaaaaaguug ccgaagauga gacugccac    1320
gcgcucagac augauaugcg gcuaugccug ccucaaaggg acugccgcca ugcggaacac  1380
caaacgaggu uccugguaca ucgaggcucu ugcucaaug uuuucugagc gggcuuguga   1440
uaugcacgug gccgacaugc ugguuaaggu gaacgcacuu aucaaggauc gggaagguua   1500
ugcuccuggc acagaauucc accggugcaa ggagaugucu gaauacugca gcacucugug     1560
ccgccaccuc uaccuguucc caggacaccc ucccacauga ugucaccucc ccaucaucca    1620
cgccaagugg aagccacugg accacaggag gugugauaga gccuugauc uucaggaugc     1680
acgguucug uucugccccc ucaggauguu ggaaucucc cagacuuguu ccugugccc       1740
aucaucucug ccuuugagug ugggacucca ggccagcucc uuuucuguga agccuuugc       1800
cuguagagcc agccuugguu ggaccuauug ccaggaaugu uucagcugca guugaagagc    1860
cugacaagug aaguuguaaa cacaguggg uuaggggag agggcauaua aauuccccau       1920
auuugguuc aguccagcu uuuguagaug gcacuuuagu gauugcuuuu auuacauuag    1980
uuaagaaguc ugagagacca ucuccuaucu uuauuucau ucauauccuc cgcccuuuu    2040
guccuagagu gagaguuugg aagguguucca aauuuaauqu agacauuauc uuuuggcucu 2100
gaagaagcaa acaugacuag agacgcaccu ugcugcagug uccagaagcg gccgugcgu    2160
ucccuucagu acugcagcgc cacccagugg aaggacacuc uuggcucguu ugggucaag    2220
gcaccgcagc cugucagcca acauugccuu gcauuugac cuuauugauc uuugcccaug   2280
gaagucucaa agaucuuucg uuggeuguguu cucugagcuu uguuacugaa augagccucg   2340
```

| | | |
|---|---|---|
| ugggagcau cagagaaggc caggaagaau ggugguguuuc ccuagacucu guaaccaccu | 2400 |
| cucugucuuu uuccuuccug agaaacgucc aucucucucc cuuacuauuc ccacuuucau | 2460 |
| ucaaucaacc ugcacuucau aucuagauuu cuagaaaagc uuccuagcuu aucucccugc | 2520 |
| uucauaucuc ucccuucuuu accuucauuu cauccuguug gcugcugcca ccaaaucugu | 2580 |
| cuagaauccu gcuuuacagg aucauguaaa ugcucaaaga uguaauguag uucuuuguuc | 2640 |
| cugcuuucuc uuucaguauu aaacucuccu uugauauuau guggcuuuua uuucagugcc | 2700 |
| auacauguua uuguuuucaa ccuagaaacc uuuauaccug cuuaucugaa acuucccaac | 2760 |
| ucccguuc uuuaagacuu uuuuuuuuu uuuuuuuuu uuugagacag agucucgcuc | 2820 |
| ugucgcccag gcuggagggc aguggcacga ucucagcuca cugcaagcuc caacucccgg | 2880 |
| guucacgcca uuccugcc ucagccuucc aaguagcugg gacuacaggu gcccgccacc | 2940 |
| gugcccggcu aauuuuuug uauuuuuagu agagacaggg uuucaccaug uuagccggga | 3000 |
| uggucuugau cuccugaccu caugauccac ccaccucagc cucccaaagu guugggauua | 3060 |
| caggcgugag ccacugcgcc cgggcaagac cuuuuuuuaa aaaaaaaaa aaaaaaacuu | 3120 |
| ccauucuuuc uucccccagu cuguucucac auaacagagu aguuuuggguu uuuaauuuuu | 3180 |
| uuugguguu ugcuguuuuu uguuuuuuaa ggugaguucu cacauguguu ucagacugg | 3240 |
| ucucgaacuc cuggccucaa gccaucuucc cgcccagcc ucaaauag cugggcuuac | 3300 |
| aggcaugagc caccaccu ggccaggauu ugguuguuua aauauaaauc ugaucacccc | 3360 |
| ccugcuuaga acccuucugc uuucuauuac cccucauuua aaauguaaac ucuucaccuu | 3420 |
| gguuuaugag aacugguucu ugccuucccc uugaaccuca uuaaauggug auuucuugcu | 3480 |
| aagcuccagc ccgaguggc uccucucagc ucuaauuuu gugcucuuuc cugcccuuuu | 3540 |
| ccugggccuu cucagcucuc caccccacc acucuugacu caggugugu ccuucuccu | 3600 |
| caagcuuga caauucccgg gcccuucagu cccugagcag ucuacuucug ugucugucac | 3660 |
| cacaucuugu cuuuucccu cauugcauuu auugcaguu auauauagc uacuuuuacu | 3720 |
| uguucauuuc ugucucccu accaggcugu aaaugagggc agaaaccuug uuuguuuau | 3780 |
| ucaccaucau guaccaagug cuggcacau aguggccuu cauuaaagu uguugaaua | 3840 |
| aaagagggaa gaaggcaagc caaccuuagc uacaauccua ccuuuugaua aaauguuccu | 3900 |
| uuugacaaua uacacggauu auuauuugua cuuuguuuuu ccauguguuu ugcuuuuauc | 3960 |
| cacuggcauu uuuagcuccu ugaagacaua ucauguguga gauaacuucc uucacaucuc | 4020 |
| ccauggu ucc uagcaaaaug cuaggccugu aguagcaag gugcucaaua aauauuuguu | 4080 |
| uggguguuu gugagccuug cugccaaguc ugccuuuugg gucgacauag uauggaagua | 4140 |
| uuugagagag agaaccuuuc cacucccacu gccaggauuu uguauugcca ucggguugcca | 4200 |
| aauaaaugcu cauauuuauu acugaaaaaa aaaaaaaaa aa | 4242 |

<210> SEQ ID NO 4
<211> LENGTH: 4057
<212> TYPE: RNA
<213> ORGANISM: Homo_sapiens
<300> PUBLICATION INFORMATION:
<308> DATABASE ACCESSION NUMBER: NM_001224.4
<309> DATABASE ENTRY DATE: 2012-12-23
<313> RELEVANT RESIDUES IN SEQ ID NO: (1)..(4057)

<400> SEQUENCE: 4

| | |
|---|---|
| agaggaagag aacgauuuaa ggagcgaaua cuacugguaa acuaauggaa gaaaucugcu | 60 |
| gcaccacugg auauugggag ugugguggcau gcauccucau caucaggaaa cucuaaaaaa | 120 |

-continued

```
gaaccgagug gugcuagcca aacagcuguu guugagcgaa uuguuagaac aucuucugga    180
gaaggacauc aucaccuugg aaaugaggga gcucauccag gccaaagugg gcaguuucag    240
ccagaaugug gaacuccuca acuugcugcc uaagaggggu ccccaagcuu uugaugccuu    300
cugugaagca cugagggaga ccaagcaagg ccaccuggag gauauguugc ucaccacccu    360
uucugggcuu cagcauguac ucccaccguu gagcugugac uacgacuuga gucucccuuu    420
uccggugugu gaguccuguc cccuuuacaa gaagcuccgc cugucgacag auacugugga    480
acacucccua gacaauaaag augguccugu cugccuucag gugaagccuu gcacuccuga    540
auuuuaucaa acacacuucc agcuggcaua agguugcag ucggccuc gugcccagc       600 acuguguug agcaaugugc acuucacugg agagaaagaa cuggaauuuc gcucuggagg    660 ggaugggag cacaguacuc uagcacccu cuucaagcuu ugggcuaug acguccaugu      720 ucuaugugac cagacugcac aggaaaugca agagaaacug cagaauuuug cacaguuacc    780
ugcacaccga gucacggacu ccugcaucgu ggcacuccuc ucgcaugggu uggagggcgc    840
cauucuaugu guggauggga aacugcucca gcuccaagag guuuuucagc ucuugacaa     900 cgccaacugc ccaagccuac agaacaaacc aaaaauguuc uucauccagg ccugccgugg    960
aggugcuauu ggaucccuug gcaccuccu ucuguucacu gcugccaccg ccucucuugc    1020
ucuaugagac ugaucguggg guugaccaac aagauggaaa gaaccacgca ggauccccug    1080
ggugcgagga gagugaugcc gguaaagaaa aguugccgaa gaugagacug cccacgcgcu    1140
cagacaugau augcggcuau gccugccuca aaggacugc cgccaugcgg aacaccaaac     1200
gagguuccug uacaucgag gcucuugcuc aaguguuucu ugagcgggcu ugugauaugc    1260
acguggccga caugcugguu aaggugaacg cacuuaucaa ggaucgggaa gguuaugcuc    1320
cuggcacaga auuccaccgg ugcaaggaga ugucugaaua cugcagcacu cugugccgcc    1380
accucuaccu guucccagga cacccuccca caugaugca ccucccauc auccacgcca     1440 aguggaagcc acuggaccac aggaggugug auagagccuu ugaucuucag gaugcacggu    1500
uucuguucug cccccucagg gaugugggaa ucucccagac uuguuccug ugccaucau     1560 cucugccuuu gagugggga cuccaggcca gcuccuuuuc ugugaagccc uuugccugua    1620 gagccagccu igguuggacc uauugccagg aauguuucag cugcaguuga agagccugac    1680
aaguuaaguu guaaacacag gugguuaug gggagagggc auauaaauuc cccauauuug    1740
uguucaguuc cagcuuuugu agauggcacu uuagugauug cuuuuauuac auuaguuaag    1800
augucugaga gaccaucucc uaucuuuuau uucauucaua uccuccgccc uuuuugccu     1860 agagugagag uuggaaggu guccaaauuu aauguagaca uuaucuuuug gcucugaaga    1920
agcaaacaug acuagagacg caccuugcug cagugucaag aagcggccug ugcguuccu    1980 ucaguacugc agcgccaccc aguggaagga cacucuuggc ucguugggc ucaaggcacc    2040 gcagccuguc agccaacauu gccuugcauu uguaccuuau ugaucuuugc ccauggaagu    2100
cucaaagauc uuucguuggu uguuucucug agcuuuguua cugaaaugag ccucugggg     2160 agcaucagag aaggccagga agaaugugu guuucccuag acucuguaac caccucucug     2220
ucuuuuuccu uccugagaaa cgccaucuc ucucccuuac uauucccacu uucauucaau     2280
caaccugcac uucauaucua gauuucuaga aaagcuuccu agcuuaucuc ccugcuucau    2340 aucucccu ucuuuaccuu cauuucaucc uguggcugc ugccaccaaa ucugucuaga      2400
auccugcuuu acaggaucau guaaaugcuc aaagauguaa guaguucuu uguuccgcu      2460 uucucuuuca guauuaaacu cuccuuugau auuaugugc uuuuauuuca gugccauaca    2520
```

| | |
|---|---|
| uguuauuguu uucaaccuag aaaccuuuau cccugcuuau cugaaacuuc ccaacuuccc | 2580 |
| uguucuuuaa gacuuuuuuu uuuuuuuuuu uuuuuuuuga cacagagucu cgcucugucg | 2640 |
| cccaggcugg agggcagugg cacgaucuca gcucacugca agcuccaacu cccggguuca | 2700 |
| cgccauucuc cugccucagc cuccaaguca gcugggacua caggugcccg ccaccgugcc | 2760 |
| cggcuaauuu uuuuguauuu uuaguagaga caggguuuca ccauguuagc cgggaugguc | 2820 |
| uugaucuccu gaccucauga uccacccacc ucagccuccc aaagug uugg gauuacaggc | 2880 |
| gugagccacu gcgcccgggc aagaccuuuu uuuaaaaaaa aaaaaaaaaa aacuuccauu | 2940 |
| cuuucuuccu ccagucuguu ucacauaac agaguaguuu ugguuuuuaa uuuuuuugg | 3000 |
| uuguuugcug uuuuuuguuu uuuaagguga guucucacua uguuucucag acugguucg | 3060 |
| aacuccuggc ucaagccau cuccccgccu cagccucuca aauagcuggg cuuacaggca | 3120 |
| ugagccacca caccuggcca ggauuugguu guuuaaauau aaaucugauc accccccugc | 3180 |
| uuagaaccu ucugcuuucu auucccccuc auuuaaaaug uaaacucuuc accuugguuu | 3240 |
| augagaacug guucuugccu uccccuugaa ccucauuaaa uggugauuuc uugcuaagcu | 3300 |
| ccagcccgag uggucuccuc ucagcuucua auuuugugcu cuuuccugcc cuuuccugg | 3360 |
| gccuucucag cucuccaccc ccaccacucu ugacucaggu ggugucccuuc uucccaagu | 3420 |
| cuugacaauu cccgggcccu ucagucccug agcagucuac uucugugucu gucaccacau | 3480 |
| cuugucuuuu ccccucauug cauuuauugc aguuauauua uaugcuacuu uuacuuguuc | 3540 |
| auuucugucu cccccuaccag gcuguaaaug agggcagaaa ccuguuugu uuuauucacc | 3600 |
| aucauguacc aagugcuugg cacauagugg gccuucauua aauguuuguu gaauaaaga | 3660 |
| gggaagaagg caagccaacc uuagcuacaa uccaccuuu ugauaaaaug uuccuuuga | 3720 |
| caauauacac ggauuauuau uugacuuug uuuuuccaug uguuugcuu uuaccacug | 3780 |
| gcauuuuuag cuccuugaag acauaucaug ugugagauaa cuuccuucac aucucccaug | 3840 |
| gucccuagca aaaugcuagg ccuguaguag ucaaggugcu caauaaauau uuguuugggu | 3900 |
| gguuugugag ccugcugcc aagccugcc uuugggucga cauaguaugg aaguauuuga | 3960 |
| gagagagaac cuuccacuc ccacugccag gauuuuguau ugccaucggg ugccaaauaa | 4020 |
| augcucauau uuauuacuga aaaaaaaaaa aaaaaaa | 4057 |

```
<210> SEQ ID NO 5
<211> LENGTH: 4024
<212> TYPE: RNA
<213> ORGANISM: Homo_sapiens
<300> PUBLICATION INFORMATION:
<308> DATABASE ACCESSION NUMBER: NM_032983.3
<309> DATABASE ENTRY DATE: 2012-12-23
<313> RELEVANT RESIDUES IN SEQ ID NO: (1)..(4024)

<400> SEQUENCE: 5
```

| | |
|---|---|
| cuuuugucug uccgccgagc accccacuuc accccauugg accgcgcggc cgccgcuaga | 60 |
| gcucugcgcc ugcgcacgca ccgggccggg gacugguugg ccugugugu gggcgcggca | 120 |
| gggcgcaggc gcaggcgcag ugugcguccg cgucugaggg gagggaugug gggaagcga | 180 |
| cggcccccgg uuuguuuggg cugugggcgg ugcgcagcgg agagcccggg aaaagcggga | 240 |
| aauggcggcg ccgagcgcgg ggucuugguc caccuuccag cacaaggagc ugauggccgc | 300 |
| ugacagggga cgcaggauau uggagagugu uggcaugcau cccaucauc aggaaacucu | 360 |
| aaaaaagaac cgagugguge uagccaaaca gcguuguug agcgaauugu uagaacaucu | 420 |
| ucuggagaag gacaucauca ccuuggaaau gagggagcuc auccaggcca aagugggcag | 480 |

-continued

| | |
|---|---|
| uuucagccag aauguggaac uccucaacuu gcugccuaag agggguccccc aagcuuuuga | 540 |
| ugccuucugu gaagccuugc acuccugaau uuuaucaaac acacuuccag cuggcauaua | 600 |
| gguugcaguc ucggccucgu ggccuagcac uggugeuugag caaugugcac ucacuggag | 660 |
| agaaagaacu ggaauuucgc ucuggagggg augeuggacca caguacucua gucacccucu | 720 |
| ucaagcuuuu gggcuaugac guccauguuc uaugugacca gacugcacag gaaaugcaag | 780 |
| agaaacugca gaauuuugca caguuaccug cacaccgagu cacggacucc ugcaucgugg | 840 |
| cacuccucuc gcaugguguu gagggcgcca ucuaugugu ggaugggaaa cugcuccagc | 900 |
| uccaagaggu uuucagcuc uuugacaacg ccaacugcc aagccuacag aacaaaccaa | 960 |
| aaauguucuu cauccaggcc ugccguggag augagacuga gcgugggguu gaccaacaag | 1020 |
| auggaaagaa ccacgcagga uccccugggu gcgaggagag ugaugccggu aaagaaaagu | 1080 |
| ugccgaagau gagacugccc acgcgcucag acaugauaug cggcuaugcc ugccucaaag | 1140 |
| ggacugccgc caugcggaac accaaacgag guuccuggua caucgaggcu cuugcucaag | 1200 |
| uguuuucuga gcgggcuugu gauaugcacg uggccgacau gcugguuaag gugaacgcac | 1260 |
| uuaucaagga ucgggaaggu uaugcuccug gcacagaauu ccaccggugc aaggagaugu | 1320 |
| cugaauacug cagcacucug ugccgccacc ucuaccuguu cccaggacac ccucccacau | 1380 |
| gaugucaccu ccccaucauc cacgccaagu ggaagccacu ggaccacagg aggugugaua | 1440 |
| gagccuuuga ucuucaggau gcacgguuuc uguucugccc ccucagggau gugggaaucu | 1500 |
| cccagacuug uuuccugugc ccaucaucuc ugccuuugag ugugggacuc caggccagcu | 1560 |
| ccuuuucugu gaagcccuuu gccuguagag ccagccuugg uuggaccauu gccaggaau | 1620 |
| guuucagcug caguugaaga gccugacaag ugaaguugua aacacagugu gguuaugggg | 1680 |
| agagggcaua uaaauuccccc auauuugugu ucaguuccag cuuuguaaga uggcacuuua | 1740 |
| gugauugcuu uuauuacauu aguuaagaug ucugagagac caucuccuau cuuuuauuuc | 1800 |
| auucauaucc uccgcccuuu uugccccuaga gugagaguuu ggaaggugec caaauuuaau | 1860 |
| guagacauua ucuuuuggcu cugaagaagc aaacaugacu agagacgcac cuugcugcag | 1920 |
| ugccagaaag cggccugugc guucccuuca guacugcagc gccacccagu ggaaggacac | 1980 |
| ucuuggcucg uuugggcuca aggcaccgca gccugucagc caacauugcc uugcauuugu | 2040 |
| accuuauuga ucuuugccca uggaagucuc aaagaucuuu cguugguugu uucucugagc | 2100 |
| uuuguuacug aaaugagccu cgugggagc aucagagaag gccaggaaga augugugguu | 2160 |
| ucccuagacu cuguaaccac cucucugucu uuuccuucc ugagaaacgu ccaucucucu | 2220 |
| cccuuacuau ucccacuuuc auucaaucaa ccugcacuuc auaucuagau uucuagaaaa | 2280 |
| gcuuccuagc uuaucccccu gcuucauauc ucccccuucu uuaccuucau uucauccugu | 2340 |
| uggcugcugc caccaaaucu gucuagaauc cugcuuuaca ggaucaugua aaugcucaaa | 2400 |
| gauguaaugu aguucuuugu uccgcuuuc ucuucaguua uuaaacucuc cuuugauauu | 2460 |
| augugguuu uauucagug ccauacaugu uauuguuuuc aaccuagaaa ccuuuauccc | 2520 |
| ugcuuaucug aaacuucca acuucccugu ucuuuaagac uuuuuuuuu uuuuuuuuu | 2580 |
| uuuuugagac agagucucgc ucugucgccc aggcuggagg gcaguggcac gaucucagcu | 2640 |
| cacugcaagc uccaacuccc ggguucacgc cauuccucug ccucagccuu ccaaguagcu | 2700 |
| gggacuacag gugcccgcca ccgugccggg cuaauuuuuu uguauuuuua guagagacag | 2760 |
| gguuucacca guguagccgg gauggucuug auccccugac cucaugaucc acccaccuca | 2820 |
| gccucccaaa guguugggau uacaggcgug agccacugcg cccgggcaag accuuuuuuu | 2880 |

```
aaaaaaaaaa aaaaaaaaac uuccauucuu ucuuccucca gucuguucuc acauaacaga    2940
guaguuuugg uuuuuaauuu uuuuugguug uuugcuguuu uuuguuuuuu aaggugaguu    3000
cucacuaugu uucucagacu ggucucgaac uccuggccuc aagccaucuu cccgccucag    3060
ccucucaaau agcugggcuu acaggcauga gccaccacac cuggccagga uuugguuguu    3120
uaaauauaaa ucugaucacc cccugcuuua gaacccuucu gcuuucuauu accccucauu    3180
uaaaauguaa acucuucacc uugguuuaug agaacugguu cuugccuucc ccuugaaccu    3240
cauuaaaugg ugauuucuug cuaagcucca gcccgagugg ucccucuca gcuucuaauu     3300 uugugcucuu uccugcccuu uuccggggcc uucucagcuc uccacccccca ccacucuuga   3360 cucaggugu guccuucuuc ucaagucuu gacaauuccc gggcccuuca gucccugagc     3420
agucuacuuc ugugcuguc accacaucuu gucuuuuccc ucauugcau uuauugcagu     3480 uuauauauau gcuacuuuua cuuguucauu ucugucuccc cuaccaggcu guaaaugagg    3540
gcagaaaccu uguuuguuuu auuccaccauc auguaccaag ugcuuggcac auagugggcc   3600
uucauuaaau guuguugaa uaaaagaggg aagaaggcaa gccaaccuua gcuacaaucc     3660
uaccuuuuga uaaaauguuc cuuuugacaa uauacggcga uuauuauuug acuuuguuu     3720 uuccaugugu uuugcuuuua uccacuggca uuuuuagcuc cuugaagaca uaucaugugu    3780
gagauaacuu ccuucacauc ucccaugguc ccuagcaaaa ugcuaggccu guaguaguca   3840
aggugcucaa uaaauauuug uuuggguggu uugugagccu ugcugccaag uccugccuuu   3900
gggucgacau aguauggaag uauuugagag agagaaccuu uccacuccca cugccaggau   3960
uuuguauugc caucgggugc caaauaaaug cucauauuua uuacugaaaa aaaaaaaaaa   4020
aaaa                                                                4024
```

<210> SEQ ID NO 6
<211> LENGTH: 452
<212> TYPE: PRT
<213> ORGANISM: Homo_sapiens
<300> PUBLICATION INFORMATION:
<308> DATABASE ACCESSION NUMBER: NP_116764.2
<309> DATABASE ENTRY DATE: 2012-12-23
<313> RELEVANT RESIDUES IN SEQ ID NO: (1)..(452)

<400> SEQUENCE: 6

```
Met Ala Ala Pro Ser Ala Gly Ser Trp Ser Thr Phe Gln His Lys Glu
1               5                   10                  15

Leu Met Ala Ala Asp Arg Gly Arg Arg Ile Leu Gly Val Cys Gly Met
                20                  25                  30

His Pro His His Gln Glu Thr Leu Lys Lys Asn Arg Val Val Leu Ala
            35                  40                  45

Lys Gln Leu Leu Leu Ser Glu Leu Leu Glu His Leu Leu Glu Lys Asp
        50                  55                  60

Ile Ile Thr Leu Glu Met Arg Glu Leu Ile Gln Ala Lys Val Gly Ser
65                  70                  75                  80

Phe Ser Gln Asn Val Glu Leu Leu Asn Leu Leu Pro Lys Arg Gly Pro
                85                  90                  95

Gln Ala Phe Asp Ala Phe Cys Glu Ala Leu Arg Glu Thr Lys Gln Gly
            100                 105                 110

His Leu Glu Asp Met Leu Leu Thr Thr Leu Ser Gly Leu Gln His Val
        115                 120                 125

Leu Pro Pro Leu Ser Cys Asp Tyr Asp Leu Ser Leu Pro Phe Pro Val
    130                 135                 140
```

Cys Glu Ser Cys Pro Leu Tyr Lys Lys Leu Arg Leu Ser Thr Asp Thr
145                 150                 155                 160

Val Glu His Ser Leu Asp Asn Lys Asp Gly Pro Val Cys Leu Gln Val
            165                 170                 175

Lys Pro Cys Thr Pro Glu Phe Tyr Gln Thr His Phe Gln Leu Ala Tyr
        180                 185                 190

Arg Leu Gln Ser Arg Pro Arg Gly Leu Ala Leu Val Leu Ser Asn Val
    195                 200                 205

His Phe Thr Gly Glu Lys Glu Leu Glu Phe Arg Ser Gly Gly Asp Val
210                 215                 220

Asp His Ser Thr Leu Val Thr Leu Phe Lys Leu Leu Gly Tyr Asp Val
225                 230                 235                 240

His Val Leu Cys Asp Gln Thr Ala Gln Glu Met Gln Glu Lys Leu Gln
            245                 250                 255

Asn Phe Ala Gln Leu Pro Ala His Arg Val Thr Asp Ser Cys Ile Val
        260                 265                 270

Ala Leu Leu Ser His Gly Val Glu Gly Ala Ile Tyr Gly Val Asp Gly
    275                 280                 285

Lys Leu Leu Gln Leu Gln Glu Val Phe Gln Leu Phe Asp Asn Ala Asn
290                 295                 300

Cys Pro Ser Leu Gln Asn Lys Pro Lys Met Phe Phe Ile Gln Ala Cys
305                 310                 315                 320

Arg Gly Asp Glu Thr Asp Arg Gly Val Asp Gln Gln Asp Gly Lys Asn
            325                 330                 335

His Ala Gly Ser Pro Gly Cys Glu Glu Ser Asp Ala Gly Lys Glu Lys
        340                 345                 350

Leu Pro Lys Met Arg Leu Pro Thr Arg Ser Asp Met Ile Cys Gly Tyr
    355                 360                 365

Ala Cys Leu Lys Gly Thr Ala Ala Met Arg Asn Thr Lys Arg Gly Ser
370                 375                 380

Trp Tyr Ile Glu Ala Leu Ala Gln Val Phe Ser Glu Arg Ala Cys Asp
385                 390                 395                 400

Met His Val Ala Asp Met Leu Val Lys Val Asn Ala Leu Ile Lys Asp
            405                 410                 415

Arg Glu Gly Tyr Ala Pro Gly Thr Glu Phe His Arg Cys Lys Glu Met
        420                 425                 430

Ser Glu Tyr Cys Ser Thr Leu Cys Arg His Leu Tyr Leu Phe Pro Gly
    435                 440                 445

His Pro Pro Thr
450

<210> SEQ ID NO 7
<211> LENGTH: 312
<212> TYPE: PRT
<213> ORGANISM: Homo_sapiens
<300> PUBLICATION INFORMATION:
<308> DATABASE ACCESSION NUMBER: NP_001215.1
<309> DATABASE ENTRY DATE: 2012-12-23
<313> RELEVANT RESIDUES IN SEQ ID NO: (1)..(312)

<400> SEQUENCE: 7

Met His Pro His His Gln Glu Thr Leu Lys Lys Asn Arg Val Val Leu
1               5                   10                  15

Ala Lys Gln Leu Leu Leu Ser Glu Leu Leu Glu His Leu Leu Glu Lys
            20                  25                  30

-continued

```
Asp Ile Ile Thr Leu Glu Met Arg Glu Leu Ile Gln Ala Lys Val Gly
             35                  40                  45

Ser Phe Ser Gln Asn Val Glu Leu Leu Asn Leu Leu Pro Lys Arg Gly
 50                  55                  60

Pro Gln Ala Phe Asp Ala Phe Cys Glu Ala Leu Arg Glu Thr Lys Gln
 65                  70                  75                  80

Gly His Leu Glu Asp Met Leu Leu Thr Thr Leu Ser Gly Leu Gln His
                 85                  90                  95

Val Leu Pro Pro Leu Ser Cys Asp Tyr Asp Leu Ser Leu Pro Phe Pro
            100                 105                 110

Val Cys Glu Ser Cys Pro Leu Tyr Lys Lys Leu Arg Leu Ser Thr Asp
        115                 120                 125

Thr Val Glu His Ser Leu Asp Asn Lys Asp Gly Pro Val Cys Leu Gln
130                 135                 140

Val Lys Pro Cys Thr Pro Glu Phe Tyr Gln Thr His Phe Gln Leu Ala
145                 150                 155                 160

Tyr Arg Leu Gln Ser Arg Pro Arg Gly Leu Ala Leu Val Leu Ser Asn
                165                 170                 175

Val His Phe Thr Gly Glu Lys Glu Leu Glu Phe Arg Ser Gly Gly Asp
            180                 185                 190

Val Asp His Ser Thr Leu Val Thr Leu Phe Lys Leu Leu Gly Tyr Asp
        195                 200                 205

Val His Val Leu Cys Asp Gln Thr Ala Gln Glu Met Gln Glu Lys Leu
    210                 215                 220

Gln Asn Phe Ala Gln Leu Pro Ala His Arg Val Thr Asp Ser Cys Ile
225                 230                 235                 240

Val Ala Leu Leu Ser His Gly Val Glu Gly Ala Ile Tyr Gly Val Asp
                245                 250                 255

Gly Lys Leu Leu Gln Leu Gln Glu Val Phe Gln Leu Phe Asp Asn Ala
            260                 265                 270

Asn Cys Pro Ser Leu Gln Asn Lys Pro Lys Met Phe Phe Ile Gln Ala
        275                 280                 285

Cys Arg Gly Gly Ala Ile Gly Ser Leu Gly His Leu Leu Leu Phe Thr
    290                 295                 300

Ala Ala Thr Ala Ser Leu Ala Leu
305                 310
```

<210> SEQ ID NO 8
<211> LENGTH: 108
<212> TYPE: PRT
<213> ORGANISM: Homo_sapiens
<300> PUBLICATION INFORMATION:
<308> DATABASE ACCESSION NUMBER: NP_116765.2
<309> DATABASE ENTRY DATE: 2012-12-23
<313> RELEVANT RESIDUES IN SEQ ID NO: (1)..(108)

<400> SEQUENCE: 8

```
Met Ala Ala Pro Ser Ala Gly Ser Trp Ser Thr Phe Gln His Lys Glu
  1               5                  10                  15

Leu Met Ala Ala Asp Arg Gly Arg Arg Ile Leu Gly Val Cys Gly Met
                 20                  25                  30

His Pro His His Gln Glu Thr Leu Lys Lys Asn Arg Val Val Leu Ala
             35                  40                  45

Lys Gln Leu Leu Leu Ser Glu Leu Leu Glu His Leu Leu Glu Lys Asp
 50                  55                  60
```

```
Ile Ile Thr Leu Glu Met Arg Glu Leu Ile Gln Ala Lys Val Gly Ser
65                  70                  75                  80

Phe Ser Gln Asn Val Glu Leu Leu Asn Leu Leu Pro Lys Arg Gly Pro
                85                  90                  95

Gln Ala Phe Asp Ala Phe Cys Glu Ala Leu His Ser
                100             105
```